United States Patent [19]

Randolph et al.

[11] Patent Number: 5,614,206

[45] Date of Patent: Mar. 25, 1997

[54] CONTROLLED DISSOLUTION PELLET CONTAINING CALCIUM SULFATE

[75] Inventors: Donald A. Randolph, Wheaton; Jodi L. Negri, Lakevilla, both of Ill.; Timothy R. Devine, Whitefish Bay, Wis.; Steven Gitelis, Oakbrook, Ill.

[73] Assignee: Wright Medical Technology, Inc., Arlington, Tenn.

[21] Appl. No.: 399,769

[22] Filed: Mar. 7, 1995

[51] Int. Cl.$^6$ ............................... A61F 2/02; A61K 9/16; A61K 9/50

[52] U.S. Cl. ........................ 424/426; 424/489; 514/951

[58] Field of Search ................................. 424/484, 423, 424/426, 489; 514/951

[56] References Cited

U.S. PATENT DOCUMENTS

| | | | |
|---|---|---|---|
| 3,279,998 | 12/1964 | Raff et al. | 167/82 |
| 3,632,739 | 1/1972 | Kornblum | 424/19 |
| 4,447,254 | 5/1984 | Hughes et al. | 71/67 |
| 4,519,801 | 5/1985 | Edgren | 604/892 |
| 4,619,655 | 10/1986 | Hanker et al. | 623/1 |
| 4,732,762 | 3/1988 | Sjogren | 424/409 |
| 4,801,458 | 1/1989 | Hidaka et al. | 424/443 |
| 4,853,225 | 8/1989 | Wahlig et al. | 424/423 |
| 4,900,546 | 2/1990 | Posey-Dowty et al. | 424/81 |
| 5,147,403 | 9/1992 | Gitelis | 623/16 |
| 5,149,368 | 9/1992 | Liu et al. | 424/602 |
| 5,262,166 | 11/1993 | Liu et al. | 424/423 |
| 5,281,265 | 1/1994 | Liu | 106/35 |

FOREIGN PATENT DOCUMENTS 0159087  10/1985  European Pat. Off. .

OTHER PUBLICATIONS

Devine et al., *Chemical Abstracts*, vol. 112, #25542, 1989.
Devine et al., "Factors Affecting Initial Strength Performance of a Hydroxylapatite–Calcium Sulfate Hemihydrate Composite," Chemical Abstracts, 1988, 112:25542.

S.F. Rosenblum et al –The Effect Of Fibroblast Growth Factor Released From A Calcium Sulfate Carrier On Bone Ingrowth Using A Canine Model –Fourth World Biomaterials Congress, p. 75 –Apr. 24–28, 1992.
Ricci et al. –Stimulation Of Bone Ingrowth Into an Implantable Chamber Through The Use Of Rapidly Resorbing Calcium Sulfate Hemihydrate –Fourth World Biomaterials Congress, p. 49 Apr. 24–28, 1992.
Hernigou et al –Diffusion Of Chemotherapeutic Agents –Rev. Chirurgie Orth. 73: pp. 517–529 (1987) (translation).
Peltier et al –Treatment of Unicameral Bone Cysts By Curettage and Packing with Plaster–of–Paris Pellets –Journal of Bone and Joint Surgery, Incorporated, vol. 60–A, No. 6 –pp. 820–822 6, Sep., 1978.
Mackey et al –Antibiotic–Impregnated Gypsum Pellets In The Surgical Management Of Chronic Osteomyelitis –International Medicine Supplement No. 9, pp. 7–9.

(List continued on next page.)

*Primary Examiner*—Carlos A. Azpuru
*Attorney, Agent, or Firm*—Fish & Richardson P.C.

[57] ABSTRACT

This invention relates to the controlled release of calcium sulfate as well as to the controlled release of an additive to a calcium sulfate matrix such as medicaments or pesticides. The controlled release is achieved by a pellet comprising calcium sulfate. The pellet is prepared by the process comprising mixing powder consisting essentially of alpha-calcium sulfate hemihydrate, a solution comprising water, and, optionally, an additive and a powder consisting essentially of beta-calcium sulfate hemihydrate to form a mixture, and forming said mixture into a pellet, wherein said alpha-calcium sulfate hemihydrate and beta-calcium sulfate hemihydrate powders have specified properties such as BET surface areas, densities, mean particle sizes, and purities. The dissolution rate of the calcium sulfate pellet is controlled by varying the weight ratio of the beta-calcium sulfate hemihydrate powder to the alpha-calcium sulfate hemihydrate powder from 0 to about 3. The invention also provides a method of delivering medicament in vivo by implanting a pellet prepared with medicament into a human or an animal.

31 Claims, 10 Drawing Sheets

OTHER PUBLICATIONS

Mackey et al –Antibiotic Loaded Plaster of Paris Pellets –Clinical Orthopaedica and Related Research –No. 167, Jul., 1982 pp. 263–268.

A. Varlet et al –Billes de plâtre de Paris aux antibiotiques dans le traitment de l'infection osseuse –Revue de Chirurqie Orthopedique, 69, 1983, pp. 239–244 (translation).

Dahners et al –Gentamicin–loaded Plaster of Paris as a Treatment of Experimental Osteomyelitis in Rabbits –Clinical Orthopaedics and Related Research –pp. 278–282 –No. 219 –Jun., 1987.

CONTROLLED DISSOLUTION PELLET CONTAINING CALCIUM SULFATE

BACKGROUND OF THE INVENTION

This invention relates to the controlled release of a calcium sulfate matrix as well as to the controlled release of an additive to the matrix such as a medicament or a pesticide. Controlled release of medication in vivo is the subject of much research. Various methods and release agents have been suggested, tested, and marketed. Calcium sulfate has been utilized as a filler for bone cavities as it is spontaneously adsorbed and replaced by bone. Calcium sulfate, formed from the hemihydrate, has been used as a controlled release agent alone for the filling of bone cavities and in combination with additives such as medicaments and pesticides. As a carrier for medicaments, it has been useful in vivo because it is biocompatible and is progressively resorbed by the body, thereby eliminating the need for secondary surgical procedures.

One application for a calcium sulfate controlled release agent is the local delivery of medicaments in vivo. The ideal characteristics of a local medicament delivery system are (1) biodegradability, (2) biocompatibility, (3) prolonged pharmaceutical release (a minimum of 4 to 6 weeks), (4) reproducibility, (5) predictable pharmacokinetics and (6) controllability. Applications include the delivery of antibiotics to bone infections, chemotherapy where surgery may be either impractical or impossible, and delivery of growth factors and analgesics. The currently acceptable methods of drug delivery are somewhat limited and unpredictable. Intravenous antibiotic therapy is the most effective route, but it requires high serum levels of drug to achieve adequately high levels at the site of infection. This can lead to serious complications in organs such as the kidneys and liver. Oral delivery of antibiotics is subject to the unpredictable nature of gastro-intestinal absorption to get the required amounts of drug to where it is needed. Delivery via implantable pumps is another method, but the pumps are invasive, must be removed, and the body may react to the presence of a foreign body at the site of infection. The most popular current method of localized delivery is the use of polymethylmethacrylate (bone cement) impregnated with antibiotics. This method allows for high tissue levels of drug being obtained without poisoning the entire system. It too has limitations, however, in that bone cement is a very dense material and is only able to deliver a limited amount of drug for a short time. In addition to this, bone cement is non-biodegradable, therefore it needs to be surgically removed at a later date, and acts as a foreign body in an infected site lending itself to other complications. Therefore, the use of calcium sulfate with its properties of biocompatibility and progressive resorption as a carrier for medicaments would be highly desirable.

The disadvantages to the use of calcium sulfate as a carrier, whether in vivo or not, however, are its rapid dissolution rate and the inability to control the rate of dissolution and, consequently, the rate of release of any additive. Various ways of controlling the rate have been attempted, for example varying the density or mass of the calcium sulfate matrix, but these methods have not been very effective.

It is therefore an object of the present invention to provide the controlled release of calcium sulfate. It is also an object to provide the controlled release of an additive such as a medicament or a pesticide which may be mixed in a calcium sulfate matrix. A further object is a method of preparing a calcium sulfate pellet with or without an additive.

SUMMARY OF THE INVENTION

The objects of the present invention are provided by a pellet having a controllable dissolution rate, wherein said pellet comprises calcium sulfate and is prepared by the process comprising:

(a) mixing powder consisting essentially of alpha-calcium sulfate hemihydrate and, optionally, powder consisting essentially of beta-calcium sulfate hemihydrate with a solution comprising water to form a mixture, and (b) forming said mixture into a pellet, wherein said powder consisting essentially of alpha-calcium sulfate hemihydrate has a purity greater than 98 wt. % calcium sulfate hemihydrate, a BET surface area in the range of from about 0.4 $m^2$/g to about 0.9 $m^2$/g, a density in the range of from about 2.73 to about 2.80 g/$cm^3$, a mean particle size of about 16 μm to about 22 μm, and wherein 90–95 wt. % of the powder consisting essentially of alpha-calcium sulfate hemihydrate has a particle size distribution from about 1 μm to about 45 μm, wherein said powder consisting essentially of beta-calcium sulfate hemihydrate has a purity greater than 98 wt. % calcium sulfate hemihydrate, a BET surface area in the range of from about 4.5 $m^2$/g to about 7.5 $m^2$/g, a density in the range of from about 2.5 g/$cm^3$ to about 2.6 g/$cm^3$, and a mean particle size in the range of from about 10 μm to about 15 μm, and wherein the dissolution rate is controlled by varying the weight milo of the powder consisting essentially of beta-calcium sulfate hemihydrate to the powder consisting essentially of alpha-calcium sulfate hemihydrate from 0 to about 3.

The alpha- and beta-calcium sulfate hemihydrate powders consist essentially of the alpha and beta crystal forms, respectively. Impurities such as calcium sulfate dihydrate may be present, but are not important to controlling the rate of dissolution of the pellet. The preferred range for the surface area of the alpha-calcium sulfate hemihydrate powder is from about 0.4 $m^2$/g to about 0.7 $m^2$/g, and for the surface area of the beta-calcium sulfate hemihydrate powder, from about 5 $m^2$/g to about 6 $m^2$/g. Preferred mean particle size for the alpha-calcium sulfate hemihydrate powder is from about 18 μm to about 22 μm, and for the beta-calcium sulfate hemihydrate powder, from about 13 μm to about 14μm. The preferred weight ratio of the beta-calcium sulfate hemihydrate powder to the alpha-calcium sulfate hemihydrate powder is in the range of from 0 to about 0.33 for the controlled release of most medicaments. Narrower ranges of this ratio, e.g., 0 to about 0.11, 0 to about 0.05, and 0 to about 0.02, are also contemplated. When used to carry growth factors, the weight ratio of the beta-calcium sulfate hemihydrate powder to the alpha-calcium sulfate hemihydrate powder may range up to about 3:1.

The invention also provides a pellet which comprises additives such as medicaments or pesticides and a method of delivering medicament in vivo by preparing the pellet with medicament and implanting it into a human or an animal. These pellets have promise as controlled release matrices where other preparations have failed.

BRIEF DESCRIPTION OF THE DRAWINGS

The advantages of the present invention will become apparent upon reading the following detailed description and upon reference to the accompanying drawings, in which.

DETAILED DESCRIPTION OF THE INVENTION

Figure 1:
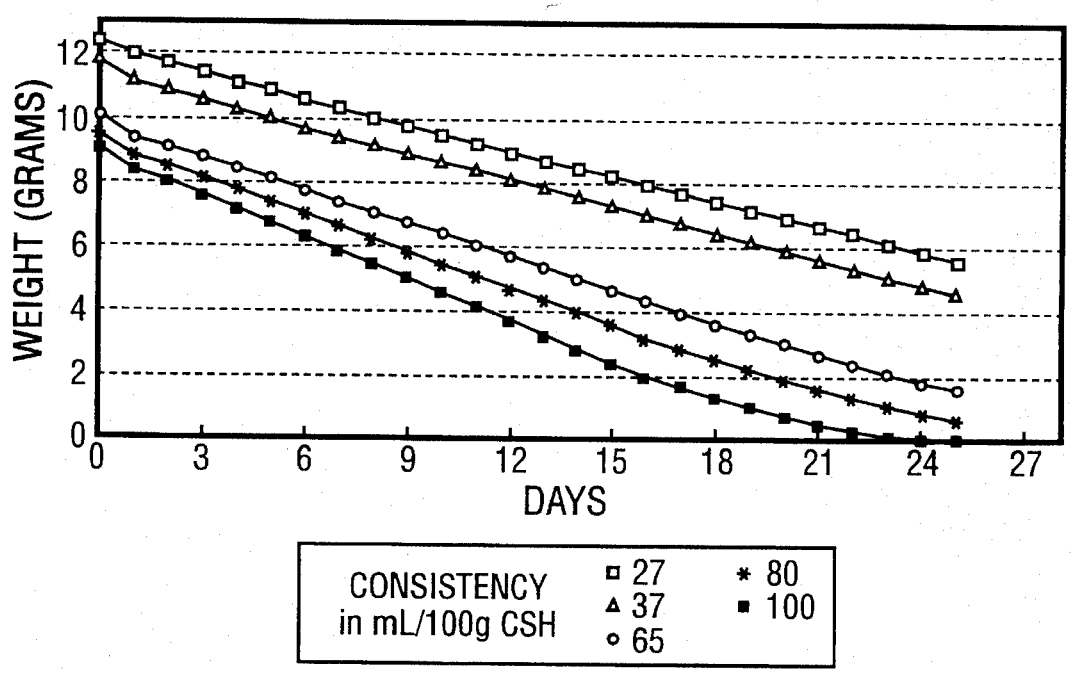
FIG. 1 shows the daily weight of the calcium sulfate ("CS") pellet dissolution with time for various calcium sulfate hemihydrate powder ("CSH") mix consistencies.

The calcium sulfate pellet of the instant invention may be used alone or as a matrix for an additive in order to control the release rate of said calcium sulfate matrix and/or additive.

The pellet is prepared by mixing alpha-calcium sulfate hemihydrate powder and, optionally, beta-calcium sulfate hemihydrate powder in a solution consisting essentially of water and then formed by molding or by applying pressure. The solution may also comprise sodium chloride, i.e., it may be a saline solution. The water to calcium sulfate hemihydrate powder weight ratio is in the range of from about 0.22 to about 1, preferably, in the range of from about 0.27 to about 0.30. The consistency of a calcium sulfate hemihydrate powder (i.e., mL solution/grams calcium sulfate hemihydrate) is proportional to its surface area and is dependent upon the morphology of the crystal. Higher surface area powders have higher water demand and will not mix or set at lower consistencies. After contact of the water or saline with the alpha- or beta-calcium sulfate hemihydrate powder, the hemihydrate is convened to the dihydrate.

If additives are desired, they may be mixed with the calcium sulfate in powdered form prior to mixing with a solution comprising water or dissolved in the solution and subsequently impregnated into the calcium sulfate powder. The additive comprises from 0 to about 25 wt. % of the pellet, preferably about 2 wt. % to about 10 wt. %, most preferably about 2 wt. % to about 5 wt. %. Examples of additives which may be mixed in the calcium sulfate matrix are medicaments or pesticides. Examples of medicaments which may be mixed with the calcium sulfate matrix are antibiotics, chemotherapeutic agents, growth factors, and analgesics. Examples of antibiotics are tetracycline hydrochloride, vancomycin, cephalosporins, and aminoglycocides such as tobramycin and gentamicin. Examples of chemotherapeutic agents are cis-platinum, ifosfamide, methotrexate, and doxorubicin hydrochloride (Adriamycin®). Examples of growth factors are transforming growth factor beta (TGF-Beta), bone morphogenic protein (BMP), basic fiberblast growth factor, platelet-derived growth factor, and other polypeptide growth factors. Examples of analgesics are anesthetics such as lidocaine hydrochloride (Xylocaine®), bipivacaine hydrochloride (Marcaine®), and non-steroidal anti-inflammatory drugs such as ketorolac tromethamine (Toradol®).

Performance of pellets made by molding or by pressing have quite comparable release profiles and dissolution rates in vivo. This lends a great deal of versatility in the ability of the material to be tailored to the needs of the particular application. The material can be pre-formed for ease of use or custom mixed or blended to meet a specific release rate or profile as specified by the surgeon in the operating room.

The following examples will show that pellets prepared from alpha-calcium sulfate hemihydrate powder with or without beta-calcium sulfate hemihydrate powder have been shown to be a controlled release system that is an effective delivery medium, both in vivo and in vitro. They will also show that the system is safe for use in vivo and effective in delivering medicament locally and in a controlled manner. High tissue levels of antibiotic were achievable for an extended period of time while maintaining a low, safe systemic effect. The other advantages of reproducibility, biodegradability and biocompatibility make this an extremely attractive in vivo system. Since the pellets are resorbable, the need for further invasive surgery for removal of the material is virtually eliminated and theoretically all of the drug is available for the application.

EXAMPLE 1

An experiment was performed to show that a calcium sulfate pellet prepared using alpha- with or without beta-calcium sulfate hemihydrate powder having specific properties can decrease the dissolution rate of a pellet.

Calcium sulfate ("CS") pellets were prepared using alpha calcium sulfate hemihydrate powder mixed at 27 and 37 mL normal saline per 100 g calcium sulfate hemihydrate powder, and beta-calcium sulfate hemihydrate powder mixed at 65, 80 and 100 mL normal saline per 100 g calcium sulfate hemihydrate powder. The mixture was allowed to wet out for 60 seconds, and then briskly mixed with a spatula for 30 seconds. Slurry was poured into cylindrical molds—2 cm diameter×2 cm height—and the 300 g Vicar set was measured on the remaining slurry. The Vicat set is a measure of the time it takes for a mixture to harden so that it may support a specific mass placed upon a needle, e.g., 300 g. Samples were allowed to hydrate approximately ten minutes beyond Vicat set, and were then demolded and weighed. The samples were dried in a 45° C. oven to constant weight. Each sample was run in triplicate. The average initial wet weights, dry weights, and Vicat set times (300 g) of the samples are given in Table 1.

TABLE 1

Sample wet and dry weights and Vicat set times.

| Sample (mL saline/ 100 g CSH) | Avg. Wet wt. (g) | Dry wt. (g) | Vicat set (min, sec) |
| --- | --- | --- | --- |
| 27 | 12.445 | 11.505 | 9'30" |
| $\sigma(n-1)$ | 0.017 | 0.017 | |
| 37 | 11.783 | 10.249 | 12'15" |
| $\sigma(n-1)$ | 0.019 | 0.013 | |
| 65 | 10.188 | 7.402 | 13'30" |
| $\sigma(n-1)$ | 0.061 | 0.056 | |
| 80 | 9.570 | 6.327 | 7'15" |
| $\sigma(n-1)$ | 0.027 | 0.019 | |
| 100 | 9.124 | 5.434 | 9'30" |
| $\sigma(n-1)$ | 0.007 | 0.005 | |

The dissolution rates of the pellets were tested by placing them in a saline solution and periodically taking them out of the solution to be weighed. The test solution was normal saline prepared by adding sodium chloride to deionized water. This saline was stirred and heated to approximately 37.8° C. on a heater/stirrer plate. Two hundred mL of the warmed saline was put into a polyethylene bottle and one cylindrical pellet added so that the pellet rested on its curved side, not on the flat surface. The bottles were labelled and placed in a water bath, maintained at 37° C. Once per day, at approximately 24 hour intervals (±90 minutes), the pellets were removed from the bottles, excess moisture removed on a paper towel, and the weights were recorded to the nearest milligram. The used saline was discarded and fresh saline, prepared as before, was placed in each bottle. The pellets were returned to bottles and the bottles to the bath.

Figure 2:
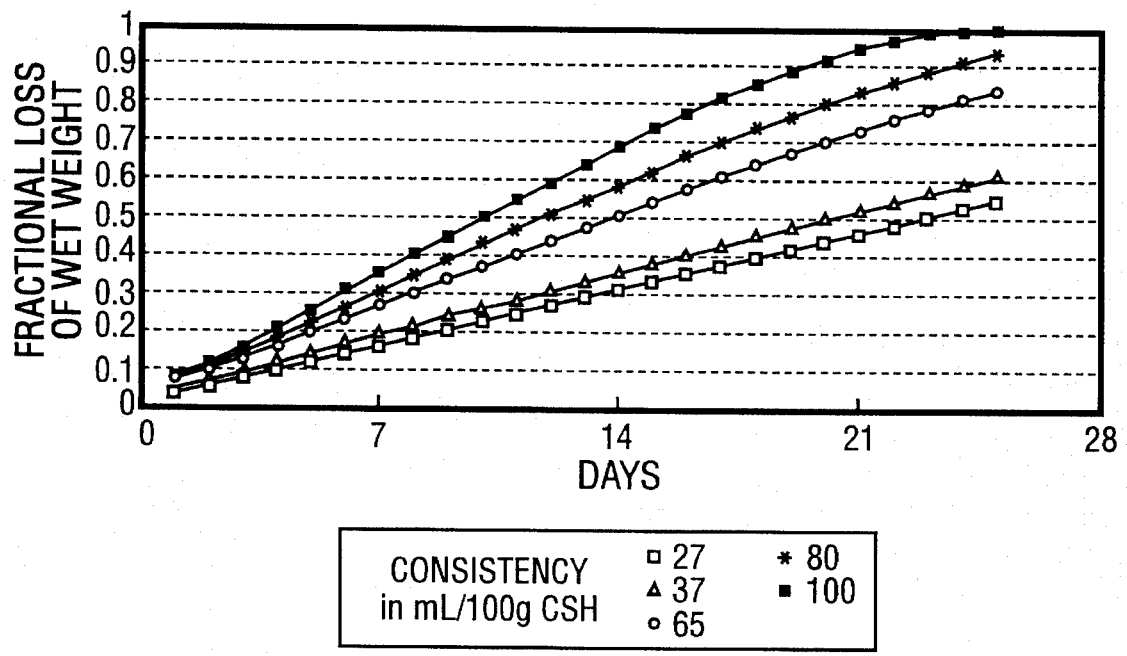
FIG. 2 shows the fractional loss of wet weight for the CS pellet dissolution with time.

FIG. 1 shows the average daily weight of each sample. FIG. 2 shows the average cumulative fractional weight loss (from the initial wet weight) and shows that the dissolution is essentially linear with time. The exceptions to the linearity in the weight loss occur on the first day and when a large fraction of the samples have dissolved. The substantial weight loss on the first day may be due to the fact that the samples were dried to constant weight prior to being immersed in saline, thus generating a somewhat larger external pellet surface area.

Figure 3:
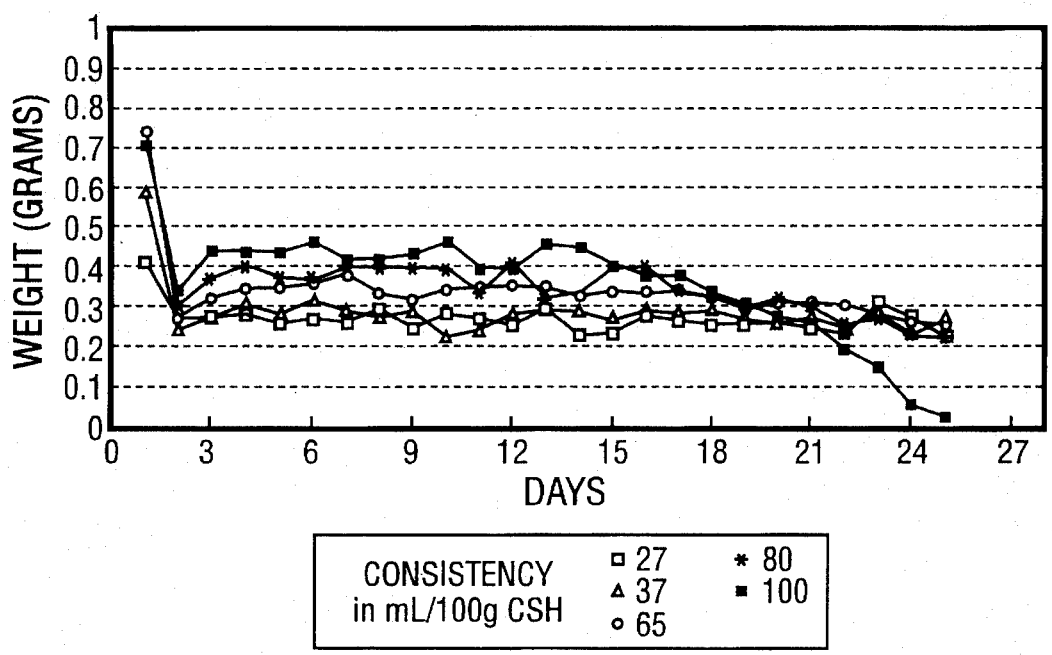
FIG. 3 shows the weight of the CS pellet daily dissolution.

The decrease in weight loss rate is particularly evident in the 100 consistency samples in the last 20% of dissolution. FIG. 3 shows the daily average weight loss for samples of each consistency. It is clear that after day 1, weight loss is quite constant (however, again noting the exception, particularly, of the 100 consistency samples at the later time periods). Table 2 gives the average daily weight loss and sample standard deviation for samples of each consistency from day 2 through day 18. From Table 2, it is apparent that the higher consistency samples had a greater absolute average daily weight loss, as well as a greater average daily fractional weight loss as seen in FIG. 2. Deviations appear to be marginally larger at the higher consistencies.

TABLE 2

Average daily weight loss

| Consistency (mL normal saline/100 g CSH) | 27 | 37 | 65 | 80 | 100 |
| --- | --- | --- | --- | --- | --- |
| Average | 0.270 | 0.281 | 0.341 | 0.372 | 0.417 |
| Sample S.D. | 0.018 | 0.023 | 0.023 | 0.034 | 0.039 |

The solubility of calcium sulfate dihydrate ("CSD") in water is approximately 0.0140 M in the temperature range of interest. This would correspond to 0.482 g of CSD per 200 mL water. It has been found that at 25° C, CSD solubility is increased by 30% relative to pure water. This would give a solubility of approximately 0.627 g per 200 mL saline. The measured decrease in the weights of the samples was substantially below this figure, except on the first day where the largest loss was in the 65 consistency samples, an average of 0.744 g. It should be noted that this weight loss contains a free water component as well as a CSD component. The above cited solubilities are not corrected for temperature. The results suggest that saturation effects were not involved in the observed dissolution rate.

The rate of dissolution is best seen from the slopes in FIG. 2. The intercepts are somewhat offset from zero due to the large dissolution observed on the first day. Linear regression analysis of the fractional weight loss data from the first 18 days of dissolution is given in Table 3.

TABLE 3

Linear regression values of the slopes and $R^2$ of FIG. 2

| Consistency mL normal saline/100 g CSH | 27 | 37 | 65 | 80 | 100 |
| --- | --- | --- | --- | --- | --- |
| Rate (% day) | 2.17 | 2.38 | 3.39 | 3.95 | 4.67 |
| $R^2$ | 0.9998 | 0.9996 | 0.9999 | 0.9996 | 0.9995 |

Figure 4:
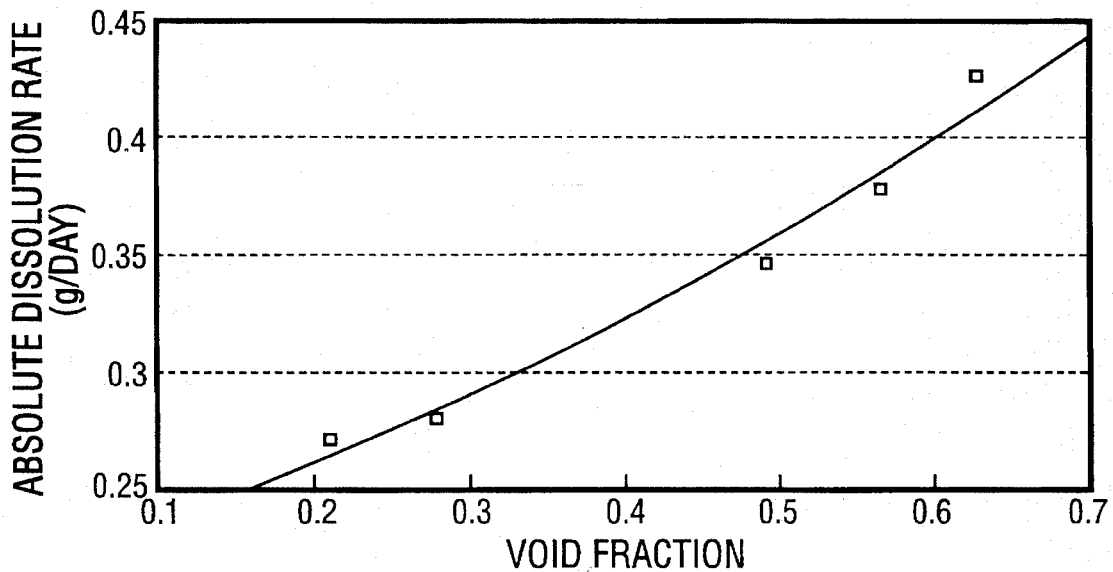
FIG. 4 shows the CS pellet dissolution rate vs. sample void fraction.

The increase in dissolution rate with consistency suggests the covariation of effective surface area. This is hardly a surprising result. However, the linear nature of these results suggests, in the reasonably assumed absence of saturation effects, that the effective surface area of the samples remains constant, even after well over a half of the sample has been dissolved. This conclusion, in turn, suggests that dissolution rate is controlled by the diffusion rate in the saline solution at 37° C. Only after approximately 80% of the sample has dissolved does the real effective surface area begin to reduce the dissolution rate. The relationship between absolute dissolution rate in g/day versus the void fraction is graphically displayed in FIG. 4. (The void fraction is calculated by subtracting the ratio of the average dry sample density to the theoretical density of CSD from one.)

Figure 5:
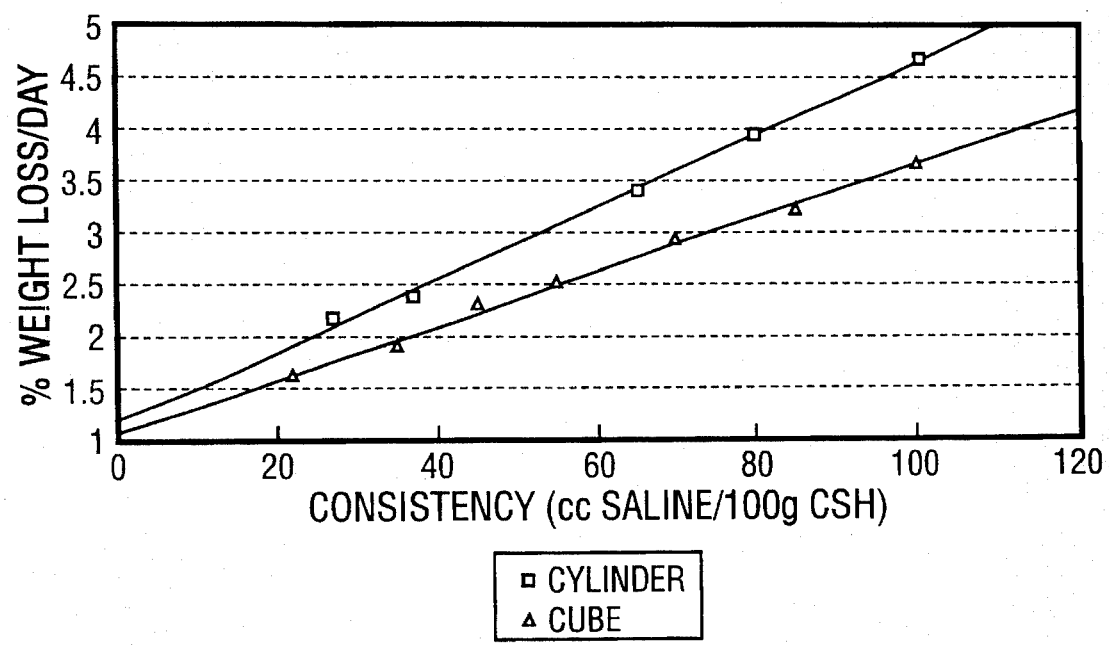
FIG. 5 shows the comparison of dissolution rates of CS pellet in saline.
Figure 6:
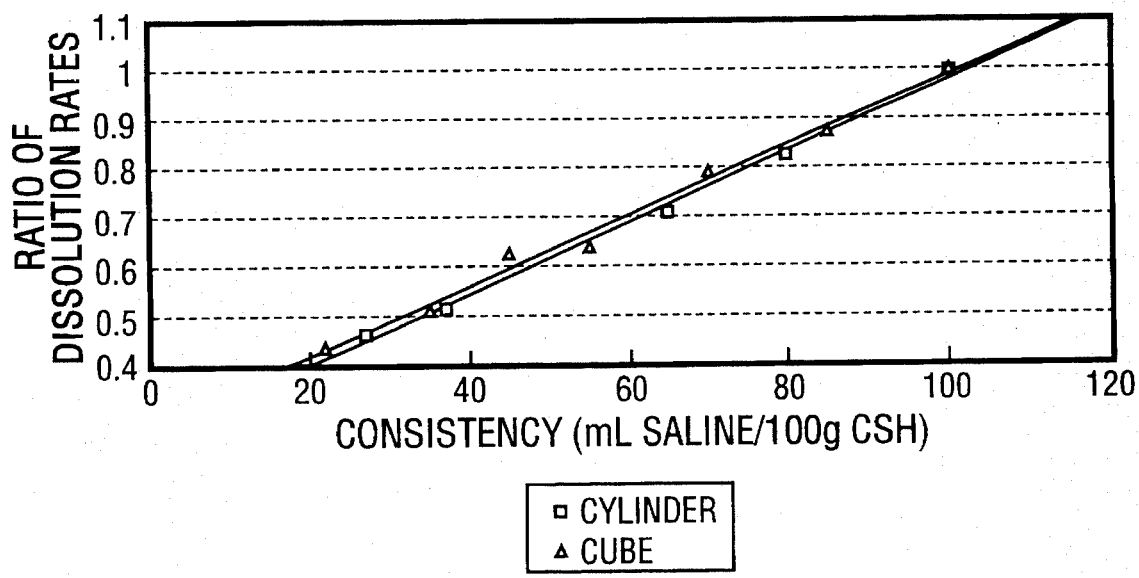
FIG. 6 shows the comparison of the cylindrical and cubic pellets.

In a related experiment, the dissolution of CSD samples in both water and saline prepared from industrial plasters comprised of alpha-calcium sulfate hemihydrate and beta-calcium sulfate hemihydrate were observed at a variety of consistencies. Consistencies greater than 40 mL/100 g CSH were prepared with beta-calcium sulfate hemihydrate and consistencies less than 40 mL/100 g CSH were prepared with alpha-calcium sulfate hemihydrate. The samples were 5.08 cm cubes. Six liters of 0.85% saline was used and the temperature was controlled at 23.9° C. FIG. 5 compares the rate of sample dissolution in saline as a function of the mix consistency for the two experiments. If, as is suggested above, diffusion is the rate controlling event, then the differences observed might be due to the higher temperature used in the present study. However, the gross sample surface area to volume ratio is substantially larger in the right circular cylinders than in the cubes. This may also enhance the fractional dissolution rate. If the data in the two sets of experiments are normed to the respective dissolution rates of the 100 consistency samples, the internal agreement of the results are apparent. This normed data is shown in FIG. 6, accompanied by linear least square fit lines.

The data show that the rate of both absolute and relative weight loss is dependent on the CSH mix consistency—the higher the consistency, the greater the rate. Therefore, the effective surface area appears to be the key to the relative rate of dissolution. The linearity of the dissolution with time suggests that the effective surface area is independent of the sample size until the sample has largely disappeared and that diffusion of the dissolved solid in solution controls the rate in the experimental protocol used.

EXAMPLE 2

An experiment was done to determine the in vitro effect of mix consistency on the rate of resorption under conditions which approximate the bodily environment. The temperature of the samples was maintained at the temperature of the human body. The water had a normal saline concentration.

Calcium sulfate ("CS") pellets were prepared with different mixtures of alpha- ("αCSH") and beta-calcium sulfate hemihydrate powder ("β-CSH"), and calcium sulfate dihydrate ("CSD") powders. The powders were mixed with normal saline or deionized water, allowed to wet out for 60 seconds and mixed briskly to form a slurry. The slurry was then spooned into the plastic mold and the material was allowed to harden into cylindrically-shaped pellets 4 cm high by 1.2 cm in diameter. The remaining slurry was used to measure the hand mixed vicat set time (300 g). The powder and solution with which the samples were prepared is as follows:

| Sample | Powder | Solution and volume | Vicat set (min, sec) |
|---|---|---|---|
| A | β-CSH | 68 mL saline/ 100 g β-CSH | 7'00" |
| B | Mixture of β-CSH and α-CSH; β-CSH/α-CSH = 2 | 55 mL saline/ 100 g α + β CSH | 11'00" |
| C | Mixture of β-CSH and α-CSH; α-CSH/β-CSH = 2 | 42 mL saline/ 100 g α + β CSH | 11'00" |
| D | α-CSH | 30 mL saline/ 100 g α-CSH | 11'00" |
| E | Mixture of α-CSH + CSD; α-CSH/CSD = 1 | 40 mL deionized water/ 200 g α-CSH + CSD | 4'00" |
| F | Mixture of α-CSH + CSD; α-CSH/CSD = 1 | 50 mL deionized water/ 200 g α-CSH + CSD | 5'00" |

Approximately ten minutes following Vicat set time, the mold was opened and the pellets removed. One hour after rehydration, the pellets were placed in an oven at 45° C. until a constant weight was achieved. The pellets were then measured dimensionally with metric calipers and weights were recorded.

The dissolution rates of the pellets were tested by placing them in a saline solution and periodically taking them out of the solution to be weighed according to the method described in Example 1.

Figure 7:
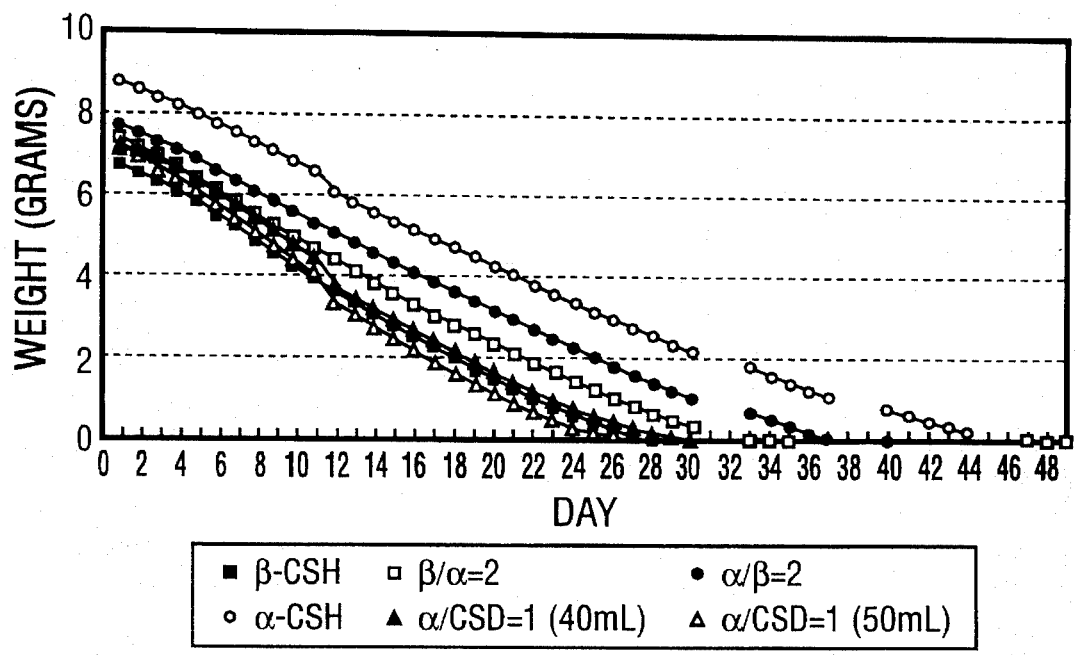
FIG. 7 shows the average daily weight of pellets in normal saline at 37° C.
Figure 8:
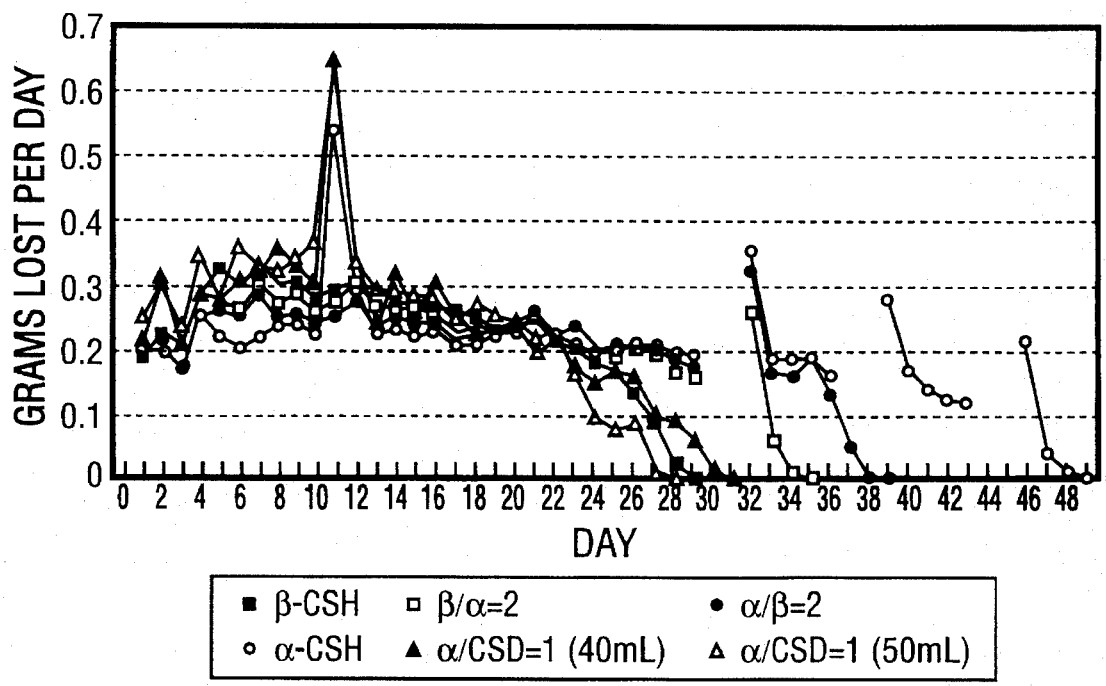
FIG. 8 shows the average loss of material per day for CS pellets in normal saline at 37° C.
Figure 9:
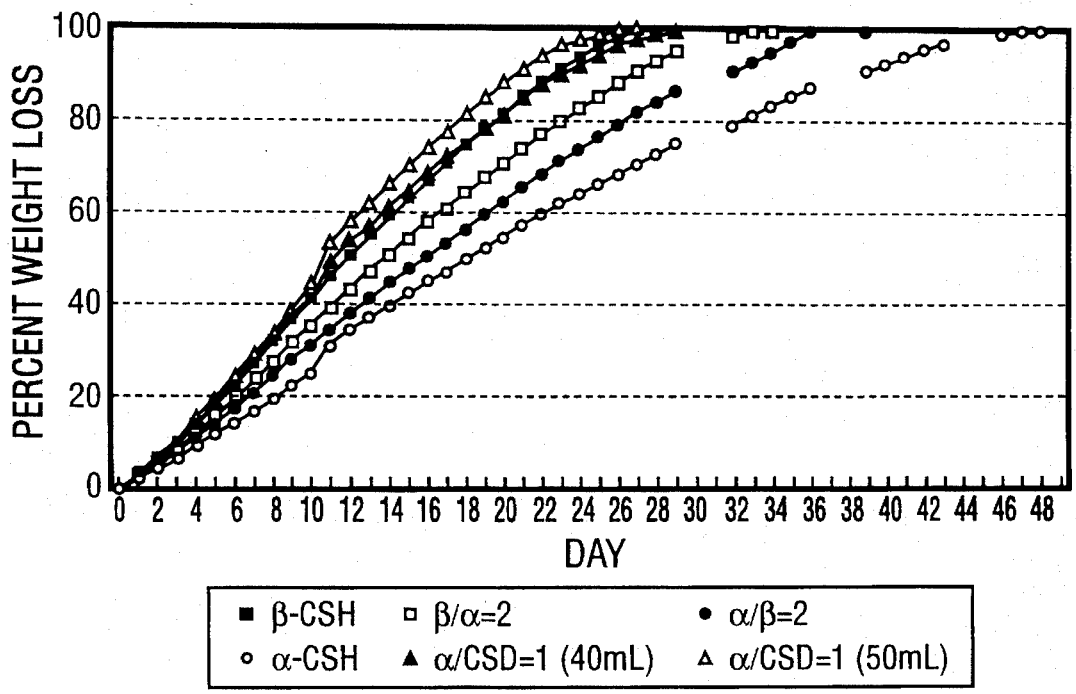
FIG. 9 shows the cumulative percent material dissolution in normal saline at 37° C.

Table 4 details dry pellet weight, height, diameter, and density. Table 5 lists the average daily weight, weight loss and cumulative percent weight loss. The values in Table 5 are illustrated in FIGS. 7, 8, and 9.

TABLE 4

Dry Pellet Data

| SAMPLE (# of pellets averaged) | | Wt. (g) | Ht. (cm) | Diam. (cm) | DENSITY (g/cm³) |
|---|---|---|---|---|---|
| A (n = 4) | AVE. | 5.1065 | 4.0124 | 1.2321 | 1.0674 |
| | S.D. | 0.0430 | 0.0051 | 0.0029 | 0.0050 |
| B (n = 5) | AVE. | 5.9393 | 4.0186 | 1.2312 | 1.2414 |
| | S.D. | 0.0579 | 0.0041 | 0.0014 | 0.0099 |
| C (n = 5) | AVE. | 6.8786 | 4.0228 | 1.2335 | 1.4309 |
| | S.D. | 0.0273 | 0.0086 | 0.0029 | 0.0074 |
| D (n = 4) | AVE. | 8.4205 | 4.0346 | 1.2449 | 1.7147 |
| | S.D. | 0.0211 | 0.0024 | 0.0007 | 0.0038 |
| E (n = 4) | AVE. | 6.3218 | 4.0148 | 1.2301 | 1.3248 |
| | S.D. | 0.0244 | 0.0035 | 0.0022 | 0.0071 |
| F (n = 4) | AVE. | 5.9640 | 4.0036 | 1.2314 | 1.2510 |
| | S.D. | 0.0317 | 0.0144 | 0.0049 | 0.0133 |

TABLE 5

Averaged data for daily weight, weight loss, and cumulative percent weight loss

| DAY | WEIGHT | Wt. Loss | % Wt. Loss | WEIGHT | Wt. Loss | % Wt. Loss | WEIGHT | Wt. Loss | % Wt. Loss |
|---|---|---|---|---|---|---|---|---|---|
| | Sample A | | | Sample B | | | Sample C | | |
| 1 | 6.7377 | | 0.0 | 7.2382 | | 0.0 | 7.7462 | | 0.0 |
| 2 | 6.5421 | 0.1956 | 2.9 | 7.0486 | 0.1896 | 2.6 | 7.5571 | 0.1890 | 2.4 |
| 3 | 6.3098 | 0.2323 | 6.4 | 6.8260 | 0.2226 | 5.7 | 7.3360 | 0.2211 | 5.3 |
| 4 | 6.1013 | 0.2085 | 9.5 | 6.6500 | 0.1760 | 8.1 | 7.1626 | 0.1734 | 7.5 |
| 5 | 5.8085 | 0.2928 | 13.8 | 6.3636 | 0.2864 | 12.1 | 6.9042 | 0.2584 | 10.9 |
| 6 | 5.4788 | 0.3297 | 18.7 | 6.0838 | 0.2798 | 15.9 | 6.6388 | 0.2654 | 14.3 |
| 7 | 5.1758 | 0.3030 | 23.2 | 5.8182 | 0.2656 | 19.6 | 6.3814 | 0.2574 | 17.6 |
| 8 | 4.8368 | 0.3390 | 28.2 | 5.5128 | 0.3054 | 23.8 | 6.0888 | 0.2926 | 21.4 |
| 9 | 4.5331 | 0.3037 | 32.7 | 5.2373 | 0.2755 | 27.6 | 5.8363 | 0.2525 | 24.7 |
| 10 | 4.2243 | 0.3088 | 37.3 | 4.9490 | 0.2883 | 31.6 | 5.5794 | 0.2569 | 28.0 |
| 11 | 3.9405 | 0.2837 | 41.5 | 4.6684 | 0.2606 | 35.2 | 5.3360 | 0.2434 | 31.1 |
| 12 | 3.6464 | 0.2941 | 45.9 | 4.4116 | 0.2768 | 39.0 | 5.0804 | 0.2556 | 34.4 |
| 13 | 2.3413 | 0.3051 | 50.4 | 4.0999 | 0.3117 | 43.4 | 4.8042 | 0.2762 | 38.0 |
| 14 | 3.0459 | 0.2954 | 54.8 | 3.8302 | 0.2697 | 47.1 | 4.5614 | 0.2428 | 41.1 |

TABLE 5-continued

Averaged data for daily weight, weight loss, and cumulative percent weight loss

| DAY | WEIGHT | Wt. Loss | % Wt. Loss | WEIGHT | Wt. Loss | % Wt. Loss | WEIGHT | Wt. Loss | % Wt. Loss |
|---|---|---|---|---|---|---|---|---|---|
| 15 | 2.7678 | 0.2781 | 58.9 | 3.5648 | 0.2654 | 50.7 | 4.3125 | 0.2489 | 44.3 |
| 16 | 2.5000 | 0.2677 | 62.9 | 3.3002 | 0.2646 | 54.4 | 4.0718 | 0.2407 | 47.4 |
| 17 | 2.2321 | 0.2679 | 66.9 | 3.0450 | 0.2552 | 57.9 | 3.8312 | 0.2406 | 50.5 |
| 18 | 1.9682 | 0.2639 | 70.8 | 2.8174 | 0.2276 | 61.1 | 3.6137 | 0.2176 | 53.3 |
| 19 | 1.7170 | 0.2513 | 74.5 | 2.5810 | 0.2364 | 64.3 | 3.3885 | 0.2251 | 56.3 |
| 20 | 1.4832 | 0.2337 | 78.0 | 2.3517 | 0.2293 | 67.5 | 3.1533 | 0.2353 | 59.3 |
| 21 | 1.2522 | 0.2310 | 81.4 | 2.1197 | 0.2320 | 70.7 | 2.9116 | 0.2417 | 62.4 |
| 22 | 0.9998 | 0.2524 | 85.2 | 1.8642 | 0.2555 | 74.2 | 2.6512 | 0.2603 | 65.8 |
| 23 | 0.7893 | 0.2105 | 88.3 | 1.6404 | 0.2238 | 77.3 | 2.4333 | 0.2179 | 68.6 |
| 24 | 0.5890 | 0.2003 | 91.3 | 1.4413 | 0.1992 | 80.1 | 2.1972 | 0.2361 | 71.6 |
| 25 | 0.4083 | 0.1807 | 93.9 | 1.2412 | 0.2001 | 82.9 | 1.9932 | 0.2041 | 74.3 |
| 26 | 0.2403 | 0.1680 | 96.4 | 1.0518 | 0.1894 | 85.5 | 1.7838 | 0.2094 | 77.0 |
| 27 | 0.1082 | 0.1321 | 98.4 | 0.8496 | 0.2022 | 88.3 | 1.5739 | 0.2099 | 79.7 |
| 28 | 0.0218 | 0.0864 | 99.7 | 0.6553 | 0.1943 | 90.9 | 1.3775 | 0.1965 | 82.2 |
| 29 | 0.0000 | 0.0218 | 100.0 | 0.4892 | 0.1661 | 93.2 | 1.1922 | 0.1853 | 84.6 |
| 30 | | | | 0.3296 | 0.1596 | 95.4 | 1.0184 | 0.1738 | 86.9 |
| 31 | | | | | | | | | |
| 32 | | | | | | | | | |
| 33 | | | | 0.0679 | 0.2617 | 99.1 | 0.6941 | 0.0343 | 91.0 |
| 34 | | | | 0.0080 | 0.0599 | 99.9 | 0.5274 | 0.1667 | 93.2 |
| 35 | | | | 0.0000 | 0.0080 | 100.0 | 0.3683 | 0.1591 | 95.2 |
| 36 | | | | | | | 0.1805 | 0.1878 | 97.7 |
| 37 | | | | | | | 0.0485 | 0.1320 | 99.4 |
| 38 | | | | | | | | | |
| 39 | | | | | | | | | |
| 40 | | | | | | | 0.0000 | 0.0485 | 100.0 |

| | Sample D | | | Sample E | | | Sample F | | |
|---|---|---|---|---|---|---|---|---|---|
| 1 | 8.8144 | | 0.0 | 7.4379 | | 0.0 | 7.1867 | | 0.0 |
| 2 | 8.6121 | 0.2023 | 2.3 | 7.2189 | 0.2191 | 2.9 | 6.9314 | 0.2553 | 3.6 |
| 3 | 8.4090 | 0.2031 | 4.6 | 6.9063 | 0.3126 | 7.1 | 6.6273 | 0.3041 | 7.8 |
| 4 | 8.2368 | 0.1723 | 6.5 | 6.6918 | 0.2145 | 10.0 | 6.3908 | 0.2365 | 11.1 |
| 5 | 7.9770 | 0.2598 | 9.5 | 6.3373 | 0.3545 | 14.8 | 6.0408 | 0.3500 | 15.9 |
| 6 | 7.7520 | 0.2250 | 12.0 | 6.0628 | 0.2745 | 18.5 | 5.7560 | 0.2847 | 19.9 |
| 7 | 7.5443 | 0.2077 | 14.4 | 5.7473 | 0.3155 | 22.7 | 5.3923 | 0.3637 | 25.0 |
| 8 | 7.3205 | 0.2237 | 16.9 | 5.4270 | 0.3203 | 27.0 | 5.0665 | 0.3258 | 29.5 |
| 9 | 7.0789 | 0.2416 | 19.7 | 5.0650 | 0.3620 | 31.9 | 4.7384 | 0.3281 | 34.1 |
| 10 | 6.8360 | 0.2429 | 22.4 | 4.7305 | 0.3345 | 36.4 | 4.3918 | 0.3466 | 38.9 |
| 11 | 6.6133 | 0.2228 | 25.0 | 4.4278 | 0.3028 | 40.5 | 4.0213 | 0.3705 | 44.0 |
| 12 | 6.0723 | 0.5410 | 31.1 | 3.7798 | 0.6480 | 49.2 | 3.3701 | 0.6511 | 53.1 |
| 13 | 5.7772 | 0.2950 | 34.5 | 3.4373 | 0.3425 | 53.8 | 3.0235 | 0.3466 | 57.9 |
| 14 | 5.5530 | 0.2242 | 37.0 | 3.2054 | 0.2318 | 56.9 | 2.7246 | 0.2990 | 62.1 |
| 15 | 5.3200 | 0.2330 | 39.6 | 2.8823 | 0.3232 | 61.2 | 2.4348 | 0.2898 | 66.1 |
| 16 | 5.0997 | 0.2203 | 42.1 | 2.6235 | 0.2588 | 64.7 | 2.1475 | 0.2872 | 70.1 |
| 17 | 4.8712 | 0.2285 | 44.7 | 2.3192 | 0.3043 | 68.8 | 1.8637 | 0.2838 | 74.1 |
| 18 | 4.6627 | 0.2085 | 47.1 | 2.0610 | 0.2581 | 72.3 | 1.6167 | 0.2470 | 77.5 |
| 19 | 4.4552 | 0.2075 | 49.5 | 1.8456 | 0.2155 | 75.2 | 1.3459 | 0.2709 | 81.3 |
| 20 | 4.2317 | 0.2235 | 52.0 | 1.6089 | 0.2366 | 78.4 | 1.0906 | 0.2553 | 84.8 |
| 21 | 4.0063 | 0.2255 | 54.5 | 1.3613 | 0.2476 | 81.7 | 0.8432 | 0.2474 | 88.8 |
| 22 | 3.7608 | 0.2455 | 57.3 | 1.1426 | 0.2187 | 84.6 | 0.6439 | 0.1993 | 91.0 |
| 23 | 3.5505 | 0.2103 | 59.7 | 0.9133 | 0.2293 | 87.7 | 0.4268 | 0.2171 | 94.1 |
| 24 | 3.3411 | 0.2094 | 62.1 | 0.7407 | 0.1726 | 90.0 | 0.2653 | 0.1615 | 96.3 |
| 25 | 3.1438 | 0.1973 | 64.3 | 0.5925 | 0.1482 | 92.0 | 0.1718 | 0.0935 | 97.6 |
| 26 | 2.9435 | 0.2002 | 66.6 | 0.4212 | 0.1713 | 94.3 | 0.0976 | 0.0742 | 98.6 |
| 27 | 2.7414 | 0.2021 | 68.9 | 0.2608 | 0.1605 | 96.5 | 0.0106 | 0.0870 | 99.9 |
| 28 | 2.5347 | 0.2067 | 71.2 | 0.1625 | 0.0982 | 97.8 | 0.0000 | 0.0106 | 100.0 |
| 29 | 2.3402 | 0.1945 | 73.4 | 0.0741 | 0.0884 | 99.0 | | | |
| 30 | 2.1492 | 0.1910 | 75.6 | 0.0137 | 0.0604 | 99.8 | | | |
| 31 | | | | | | | | | |
| 32 | | | | | | | | | |
| 33 | 1.7963 | 0.3529 | 79.6 | 0.0000 | 0.0137 | 100.0 | | | |
| 34 | 1.6118 | 0.1845 | 81.7 | | | | | | |
| 35 | 1.4251 | 0.1867 | 83.8 | | | | | | |
| 36 | 1.2389 | 0.1862 | 85.9 | | | | | | |
| 37 | 1.0796 | 0.1593 | 87.8 | | | | | | |
| 38 | | | | | | | | | |
| 39 | | | | | | | | | |
| 40 | 0.8024 | 0.2772 | 90.9 | | | | | | |
| 41 | 0.6323 | 0.1701 | 92.8 | | | | | | |
| 42 | 0.4942 | 0.1381 | 94.4 | | | | | | |
| 43 | 0.3733 | 0.1209 | 95.8 | | | | | | |
| 44 | 0.2564 | 0.1169 | 97.1 | | | | | | |
| 45 | | | | | | | | | |
| 46 | | | | | | | | | |

TABLE 5-continued

Averaged data for daily weight, weight loss, and cumulative percent weight loss

| DAY | WEIGHT | Wt. Loss | % Wt. Loss | WEIGHT | Wt. Loss | % Wt. Loss | WEIGHT | Wt. Loss | % Wt. Loss |
|---|---|---|---|---|---|---|---|---|---|
| 47 | 0.0438 | 0.2125 | 99.5 | | | | | | |
| 48 | 0.0054 | 0.0384 | 99.9 | | | | | | |
| 49 | 0.0000 | 0.0054 | 100.0 | | | | | | |

Two water baths were required to maintain all the pellets at 37° C. On day 11 of the experiment, a malfunction was noted in one bath which caused an increase in temperature to 50° C. The result was an increase in material dissolution as seen in FIGS. 7, 8 and 9 for Samples E and F. The problem was resolved and the pellets returned to the original dissolution rates as can be seen by the slopes in the figures. Interruptions are seen where materials were allowed to stand over weekend periods without changing solutions near the conclusion of the study. Again slopes and rates returned to the same "pace" as they had originated from after the saline solutions were changed.

As was the case in Example 1, material dissolution was linear through the first 80% of each of the pellets' weight loss and the rates tended to fail off somewhat in the last 20% of dissolution. Table 6 shows the average daily weight loss and linear regression of the percent weight loss for the initial 80% of dissolution of each of the six types of pellets. This further illustrates how the pellets of the instant invention prepared using alpha-CSH with or without beta-CSH (Samples B, C, and D) have longer dissolution profiles than do the pellets prepared with beta-CSH (Sample A) or with alpha-CSH and CSD (Samples E and F).

TABLE 6

Average daily weight loss and standard deviation, rate, and correlation coefficient for Samples A–F through 80% of dissolution

| | Sample A | Sample B | Sample C | Sample D | Sample E | Sample F |
|---|---|---|---|---|---|---|
| Average Daily Weight Loss (grams) | 0.2743 | 0.2520 | 0.2374 | 0.2298 | 0.3038 | 0.3245 |
| Standard Deviation | 0.0380 | 0.0347 | 0.0264 | 0.0632 | 0.0918 | 0.0883 |
| Rate of Loss (%/day) | 4.25 | 3.62 | 3.54 | 2.71 | 4.33 | 4.77 |
| Correlation Coefficient ($R^2$) | 0.9985 | 0.9986 | 0.9976 | 0.9963 | 0.9952 | 0.9956 |

Figure 10:
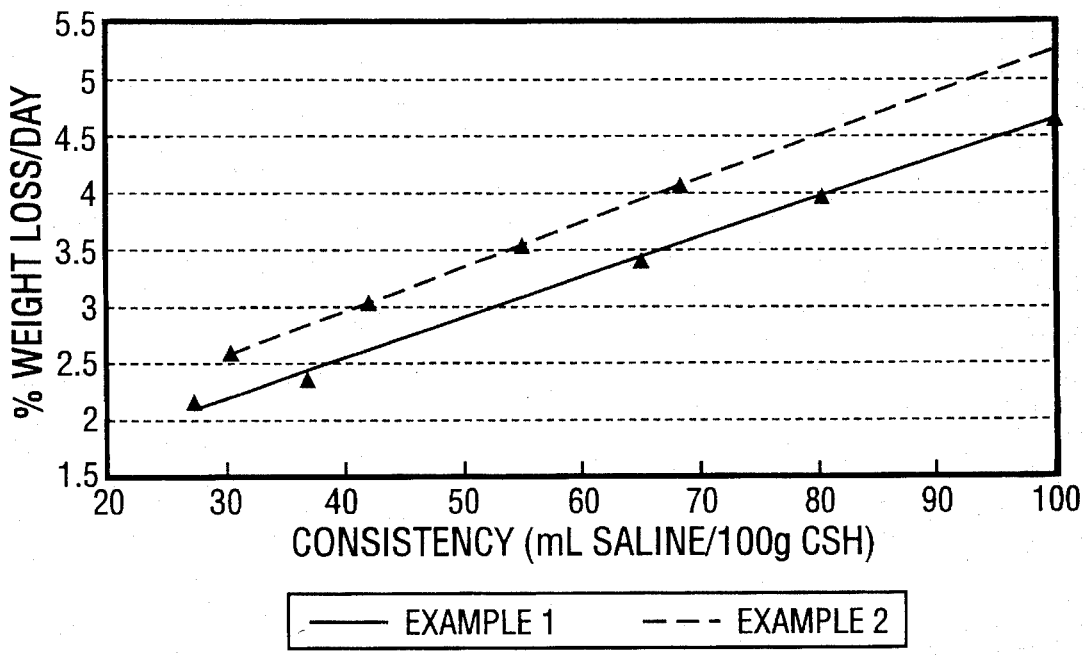
FIG. 10 shows a comparison between dissolution rates of materials in Examples 1 and 2.

FIG. 10 further compares the results of this study with those of Example 1 where cylindrical casts were evaluated for dissolution rates in 0.9% saline at 37° C. The only significant differences between the two studies are the hemihydrate bases evaluated and the surface area to volume ratios of the cylinders cast. Clearly the slopes are the same and, in fact, the correlation coefficient of the two sets of data is 1.00.

All formulations have shown consistent and predictable behavior throughout the experiment. The results suggest pellets prepared using the alpha- with or without beta-CSH materials can be custom designed to control the dissolution rate, and thus the release rate of any additive, in vivo or in vitro, and that resorption in vivo can be tailored to meet a specific demand or application by particular selection of medical grade base material and use consistency.

EXAMPLE 3

In Vitro Study: Tetracycline Hydrochloride. A one gram pellet was prepared by the procedure of Example 1 except that the calcium sulfate hemihydrate powder was alpha only and contained medicament and a solution of pure water was used instead of saline. Alpha-calcium sulfate hemihydrate powder (800 mg) was dry mixed with approximately 200 mg of tetracycline hydrochloride. The dry mixture was then added to 0.25 mL pure water and formed into a pellet by applying pressure (approximately 50 psi for about 5 minutes). The pellet was composed of 80 wt. % alpha-calcium sulfate hemihydrate powder and 20 wt. % tetracycline hydrochloride. The pellet was placed in 120 mL of deionized water in a plastic jar suspended in a 37° C. water bath. The water was changed periodically. When the water was changed, the pH was measured and aliquot samples taken for visible/uv absorbance spectroscopy to determine the amount of tetracycline in solution.

Aliquot soak time, cumulative soak time, pH, milligrams of tetracycline, percent of the original tetracycline, and cumulative percent of tetracycline are reported in Table 7. The absorbance peak at 357 nanometers was used to determine the concentration of tetracycline by comparing with standards. The variation in pH adds some uncertainty to the percentages presented.

TABLE 7

In vitro Release of Tetracycline Hydrochloride

| Aliquot Soak (hours) | Cumulative (hours) | pH | TC (mg) | % of original | Cumulative % |
|---|---|---|---|---|---|
| 60 | 60 | 3.8 | 13.1 | 6.55 | 6.55 |
| 24 | 84 | 5.4 | 3.1 | 1.55 | 8.11 |
| 30 | 114 | 5.4 | 4.1 | 2.05 | 10.16 |
| 24 | 138 | 5.4 | 7.7 | 3.85 | 14.01 |
| 24 | 162 | 5.5 | 4.2 | 2.08 | 16.09 |
| 72 | 234 | 5.5 | 10.0 | 5.00 | 21.10 |
| 24 | 258 | 6.7 | 2.7 | 1.35 | 22.44 |
| 24 | 282 | 5.4 | 2.5 | 1.24 | 23.69 |
| 23 | 305 | 5.8 | 3.3 | 1.63 | 25.32 |
| 24 | 329 | 6.2 | 4.8 | 2.40 | 27.72 |
| 108 | 437 | 6.1 | 5.3 | 2.65 | 30.37 |
| 48 | 485 | 6.4 | 1.5 | 0.75 | 31.12 |

These results indicate that a sustained release of a medicament in a localized area from a calcium sulfate matrix over an extended period of time is achievable.

EXAMPLE 4

In Vivo Study: Tobramycin Sulfate in Rats. Fourteen pellets were prepared by the procedure of Example 3 except that the medicament was tobramycin sulfate. Table 8 gives the physical dimensions, weights and densities of the individual pellets. The reproducibility as seen in the standard deviations seems acceptable for an experimental process.

TABLE 8

Tobramycin Sulfate in a
Calcium Sulfate Matrix: Physical Properties

| Pellet # | Length (mm) | Diam. (mm) | Volume (cm³) | Weight (mg) | Density (g/cm³) |
|---|---|---|---|---|---|
| 1 | 9.8 | 6.40 | 0.315 | 669.3 | 2.123 |
| 2 | 9.8 | 6.38 | 0.313 | 669.5 | 2.137 |
| 3 | 9.6 | 6.40 | 0.309 | 654.0 | 2.118 |
| 4 | 9.9 | 6.40 | 0.318 | 676.6 | 2.124 |
| 5 | 9.8 | 6.39 | 0.314 | 669.1 | 2.219 |
| 6 | 9.7 | 6.41 | 0.313 | 677.1 | 2.163 |
| 7 | 10.0 | 6.42 | 0.324 | 687.2 | 2.123 |
| 8 | 9.7 | 6.38 | 0.310 | 658.5 | 2.124 |
| 9 | 9.8 | 6.39 | 0.314 | 676.6 | 2.153 |
| 10 | 9.9 | 6.41 | 0.319 | 659.8 | 2.065 |
| 11 | 9.7 | 6.40 | 0.312 | 661.5 | 2.120 |
| 12 | 10.0 | 6.40 | 0.322 | 688.7 | 2.141 |
| 13 | 10.0 | 6.41 | 0.323 | 679.0 | 2.104 |
| 14 | 9.9 | 6.41 | 0.319 | 684.0 | 2.141 |
| Average | 9.83 | 6.40 | 0.316 | 672.2 | 2.126 |
| S.D.(n − 1): | 0.13 | 0.01 | 0.005 | 11.0 | 0.023 |

Figure 11:
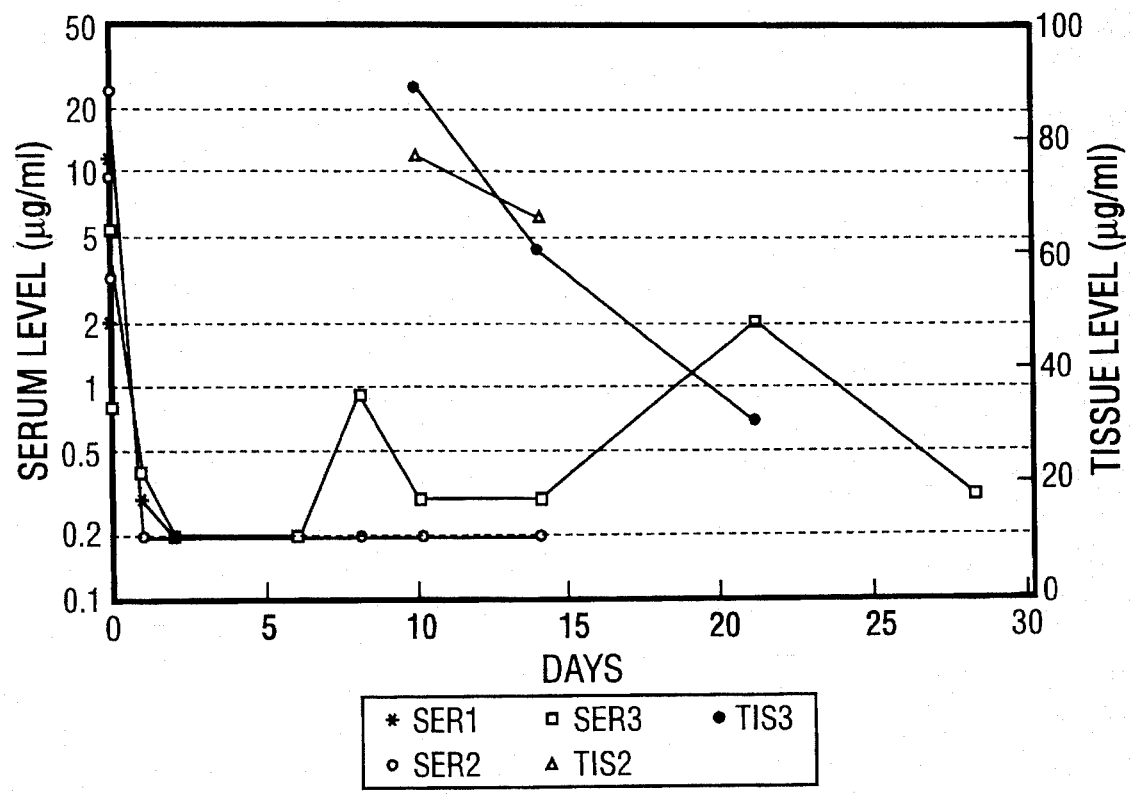
FIG. 11 shows the daily levels of tobramycin in the serum and tissue.

Pellets were implanted in three Sprague Dowley rats and serum and tissue levels of the tobramycin were monitored. The results from the experiment are presented in FIG. 11. The duration of release is well matched to the needs of this type of medication. The low systemic (serum) levels and high local (tissue) concentration make this a particularly satisfactory method of antibiotic release in instances of surgical repair or removal of tissue, or as an adjunct to implant procedures.

The results of Examples 3 and 4 show the ability to form calcium sulfate pellets for sustained and controlled release of tetracycline hydrochloride and tobramycin sulfate using alpha-calcium sulfate hemihydrate powder. These results indicate that a sustained release of a medicament in a localized area from a calcium sulfate matrix while maintaining a very low level of medication in the blood over an extended period of time is achievable.

EXAMPLE 5

In Vivo Study: Pressed Versus Molded Implants. A study was done to see whether the release rate was dependent upon the pellet preparation method. Pellets were prepared by both pressed and molded methods to a consistency of 37 mL water/100 g alpha-calcium sulfate hemihydrate powder.

Pressed Pellets: The pressed pellets were produced by starting with a dry blend of 83.4656 grams of alpha-calcium sulfate hemihydrate powder, 2.0425 grams of tobramycin sulfate and 1.0052 grams of fresh ground calcium sulfate dihydrate mixed thoroughly for ten minutes. A pellet punch and die were used to form the pellets by adding 1.75 grams of the powder blend to 472 µL of sterile saline (as measured with a Model V200TE variable volume pipette, Ulster Scientific, Inc.), stirring to a uniform consistency and allowing the mix to rest for five minutes. A Carver Laboratory Press (Model M) was then used to compress the pellets @50 psi until the mix had hardened (5 minutes) and could be ejected from the die. Thirty minutes after initial hydration, the pellets were placed in an oven at 45° C. and dried to constant weight. The final pellets had average cylindrical dimensions of 9.63 mm in height and 11.15 mm in diameter with a 2 wt. % loading of tobramycin (approximately 40 mg). A total of 30 pellets were manufactured in this way for the study. The implants were then individually weighed, measured and packaged to be secondarily sterilized by 2.5 megarads of gamma irradiation.

Molded Pellets: It was determined by temperature rise studies that the material would be substantially hydrated at the 30 minute point (Vicat Set at approximately 6 minutes) using the techniques and mixing consistency outlined below. The molded implants were produced in the operating room at the time of the animal experimentation. For this procedure, packages containing 50.0 grams of alpha-calcium sulfate hemihydrate powder and 1.20 gram vials of tobramycin sulfate had been provided from the same corresponding lots as were used for the pressed implants. These materials were sterilized in their individual packages by exposure to 2.5 megarads of gamma irradiation.

The pellet molding was carried out as follows. A 1.20 gram vial of the water soluble tobramycin sulfate was mixed into 15 mL of sterile water. A 50.0 gram package of alpha-calcium sulfate hemihydrate powder was then added to the solution and mixed by hand in a small mixing bowl until a smooth uniform consistency was achieved. This mix was then placed in the mold and allowed to stand for twenty minutes until the mold could be separated and the implants removed. Three implants were made by this process which yielded a 2 wt. % loading of tobramycin sulfate (approximately 170 mg per implant). Table 9 shows the results of this test for three pellets immediately after they were demolded (approximately 20 minutes after mixing began).

TABLE 9

Molded pellet properties
immediately after removal from the mold

| PELLET # | WEIGHT (grams) | HEIGHT (cm) | DIAMETER (cm) | DENSITY (g/cm³) |
|---|---|---|---|---|
| 1 | 8.8499 | 4.059 | 1.200 | 1.928 |
| 2 | 8.8403 | 4.054 | 1.204 | 1.915 |
| 3 | 8.9313 | 4.090 | 1.202 | 1.924 |
| AVERAGE | 8.8738 | 4.068 | 1.202 | 1.923 |
| STAN. DEV. | 0.0408 | 0.016 | 0.002 | 0.005 |

The pellets were then dried at 45° C. until a constant weight was obtained and the results are shown in Table 10.

TABLE 10

Molded pellets after drying to constant weight

| PELLET # | WEIGHT (grams) | HEIGHT (cm) | DIAMETER (cm) | DENSITY (g/cm³) |
|---|---|---|---|---|
| 1 | 8.02 | 4.059 | 1.200 | 1.74 |
| 2 | 8.04 | 4.054 | 1.204 | 1.74 |
| 3 | 8.10 | 4.090 | 1.202 | 1.74 |
| AVERAGE | 8.05 | 4.068 | 1.202 | 1.74 |
| STAN DEV. | 0.03 | 0.016 | 0.002 | 0.00 |

Tables 9 and 10 show a uniform and consistent product.

A proof-of-principal animal study was run as per the following protocol:

1) Six mixed breed male dogs (approximately 25 kg each) were implanted with the pellets prepared with alpha-calcium sulfate hemihydrate powder and tobramycin:

a) Three dogs using four pre-manufactured, pressed pellets per dog.

b) Three dogs using one pellet molded in the operating room as described above.

2) The animals have had both tissue and serum samples taken for tobramycin levels at hours 1, 3, and 24 and at days 2, 3, 5, 7, 14, 21, 28, 35, and 42.

3) Radiographs were taken at days 0 (post-operatively), 11, 28, and 35.

4) At day 42, the experiment was terminated to assess the local tissue response to the implants.

Each procedure took approximately 30–40 minutes to perform. The surgery involved making a small incision (approximately 5 cm long) over the left anterior, proximal end of the humerus and the coveting tissue was then resected to expose the bone. A pilot hole, approximately 2 mm in diameter, was drilled into the longitudinal axis of the bone. This was subsequently enlarged to a diameter of 13 mm at a depth of about 4 to 5 cm to allow sufficient space for the pellets to be implanted.

The first three dogs were implanted with four pre-manufactured pressed pellets each, stacked in such a way as to cream a large cylinder. After the pellets were in place, the implants were covered by suturing the soft tissue over the hole and finally suturing the skin. Anterior-posterior and lateral radiographs were taken to view the implants following surgery. It was interesting to note that, on the third dog, the x-ray clearly showed that the second most proximal pellet had rotated 90° so that the side (curved edge) of the cylinder was in contact with the flat surface of the pellet below.

For the final three dogs, access to the bone implant site was gained using the same procedure as was used for the pressed pellets. The implants in this case, however, were made on site using the molding technique developed as described previously. The surgery proceeded as in the case of the pressed pellets and again pest surgical radiographs were taken. There was a definite distinction noted in the x-rays in the density of the two types of implants used. In the molded implants, some small voids could be detected in the x-rays, but it was difficult to identify whether they were on the surface or internal.

All of the animals completed the six weeks of experimentation with no surgical complications or adverse reactions. Both the serum and tissue tobramycin levels were monitored throughout the experimentation. The tobramycin assay was done utilizing fluorescence, polarization, immunoassay technology. Serum levels were determined by submitting 3 to 5 mL samples of blood drawn from the dorsum of the limb via venipuncture for analysis. Samples were taken pre-operatively (as controls) as well as when outlined above. X-ray control was used after day 11 to monitor the positioning of the hypodermic needle with respect to the implants for aspiration of samples for serum and tissue tobramycin levels. This was necessary since it was noted that sample collection technique was critical to maintaining consistency in the results of the experiment.

Figure 12:
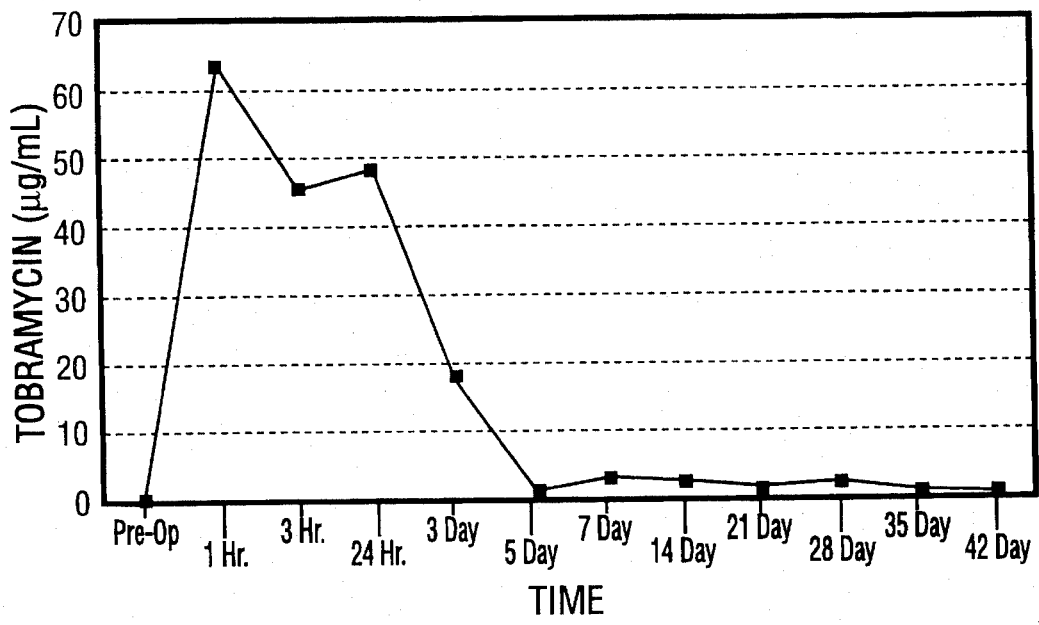
FIG. 12 shows the average tissue tobramycin levels for all implants.
Figure 13:
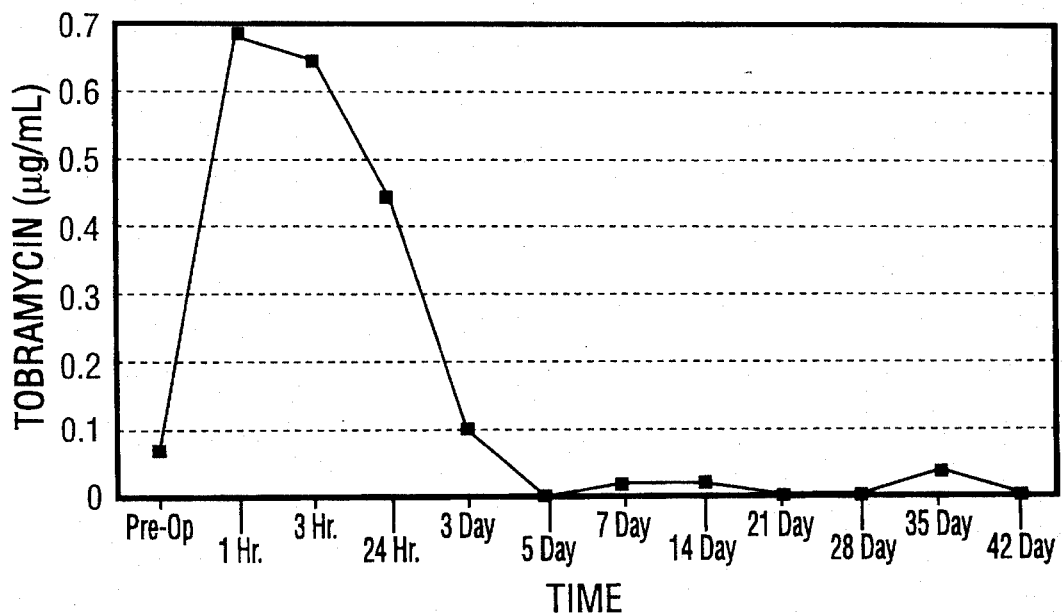
FIG. 13 shows the average serum tobramycin levels for all implants.

The average tobramycin levels for all six animals in the tissue assays are shown in FIG. 12. Starting from time zero, there is a maximum rise of tissue tobramycin to greater than 60 μg/mL @ hour 1 which slowly declines to approximately 45 μg/mL @ hours 3 and 24. A steady decline is noted from hour 24 to day 5 until a fairly steady state appears for the duration of the experiment (1 to 3 μg/mL). The serum level profile (FIG. 13) is similar to that of the tissue level but at a much lower level. Starting at time zero, a maximum serum level of 0.7 μg/mL is reached and maintained through hour 3 and then steadily declines to 5. From 5 to 42, less than 0.1 μg/mL of tobramycin is detected in the serum and, in many cases, there was no detectable amount present within the serum.

Figure 14:
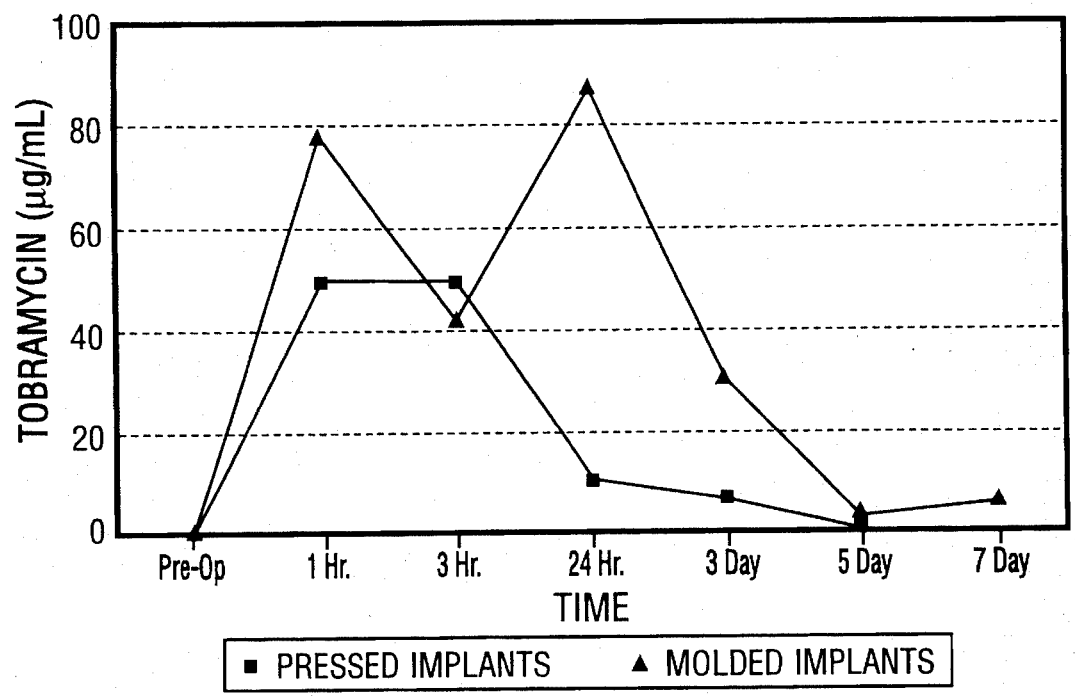
FIG. 14 shows the initial tobramycin tissue levels of pressed vs. molded implants.
Figure 15:
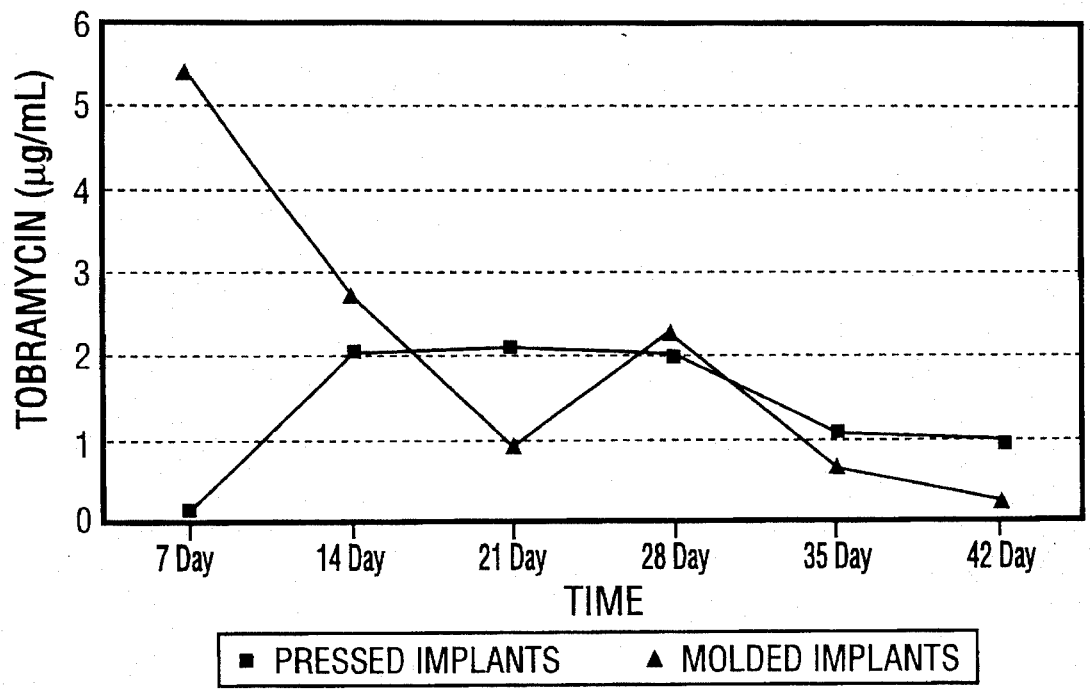
FIG. 15 shows the steady state tobramycin tissue levels of pressed vs. molded implants.
Figure 16:
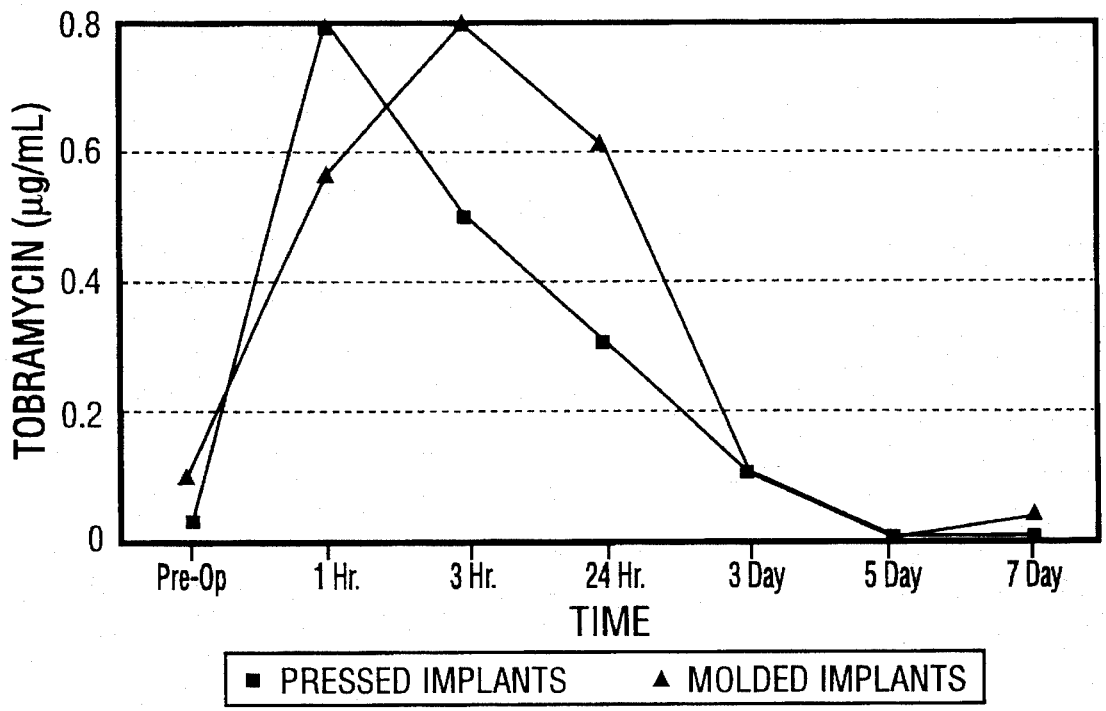
FIG. 16 shows the initial tobramycin serum levels of pressed vs. molded implants.
Figure 17:
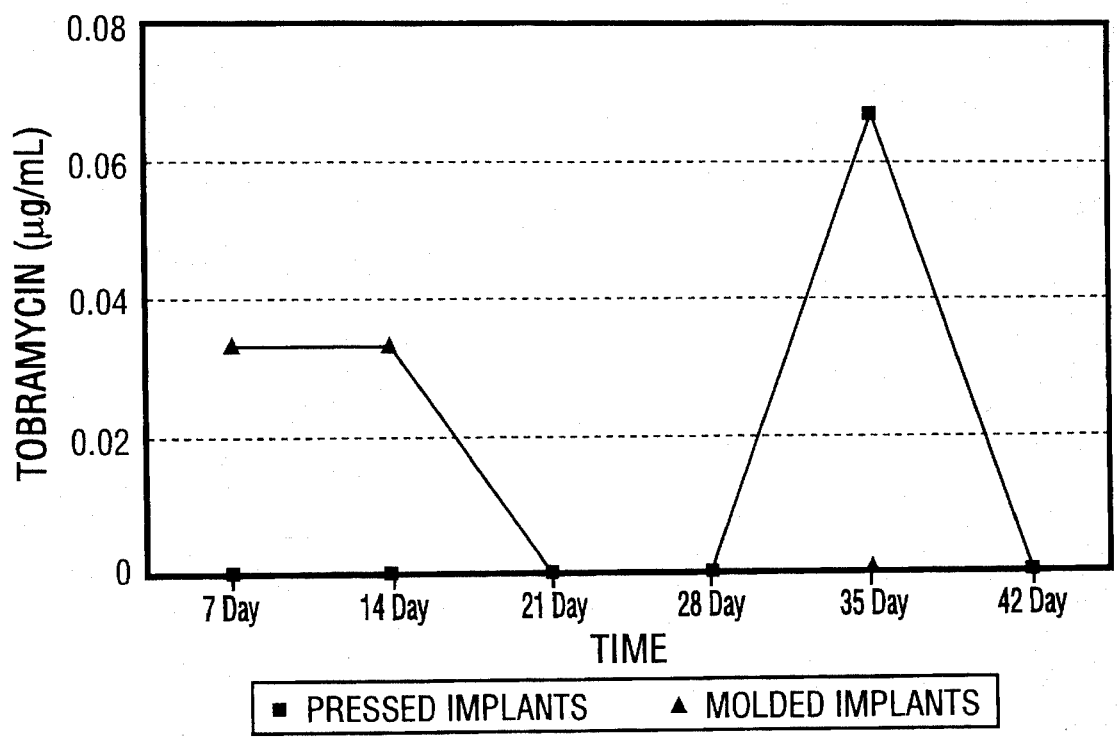
FIG. 17 shows the steady state tobramycin serum levels of pressed vs. molded implants.

A breakdown comparison between the pressed and molded implants at the tissue levels shows similar profiles. The molded implants exhibit a higher initial rise to about 90 μg/mL and a steady decline to day 5 (FIG. 14) to a relatively constant level for days 7 through 42 (FIG. 15). The pressed implants show similar profiles with a lower initial rise to about 50 and again the same decline and steady state. FIGS. 16 and 17 show the corresponding serum levels of tobramycin for the two types of implants.

Figure 18:
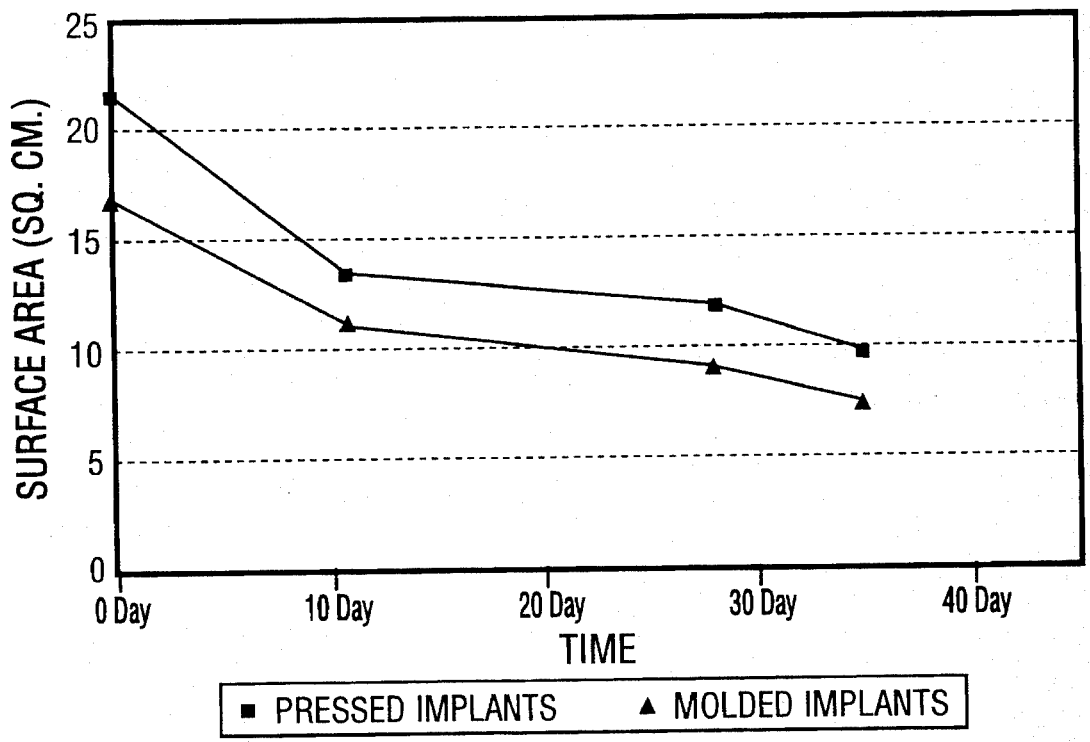
FIG. 18 shows the implant surface area vs. time.

Radiographs were used to monitor implant resorption trends over the course of the experiment. Measurements were taken from the two dimensional x-rays and converted to surface area in $cm^2$. Due to magnification in the image, the values were normalized to reflect actual sizes based on the starting, known dimensions. A plot of surface area vs. time is shown in FIG. 18, and it can clearly be seen that resorption profiles of the two types of implants follow the same trend throughout the course of the study.

The experiment was run at relatively low levels of tobramycin (approximately 160 to 170 rag/procedure) in comparison to current surgical procedures where as much as 1 to 2 grams of drug may be mixed with bone cement for implantation. It is possible to use a higher level of loading of drug (on the order of 5 wt. %) to achieve an even greater effect.

Figure 19:
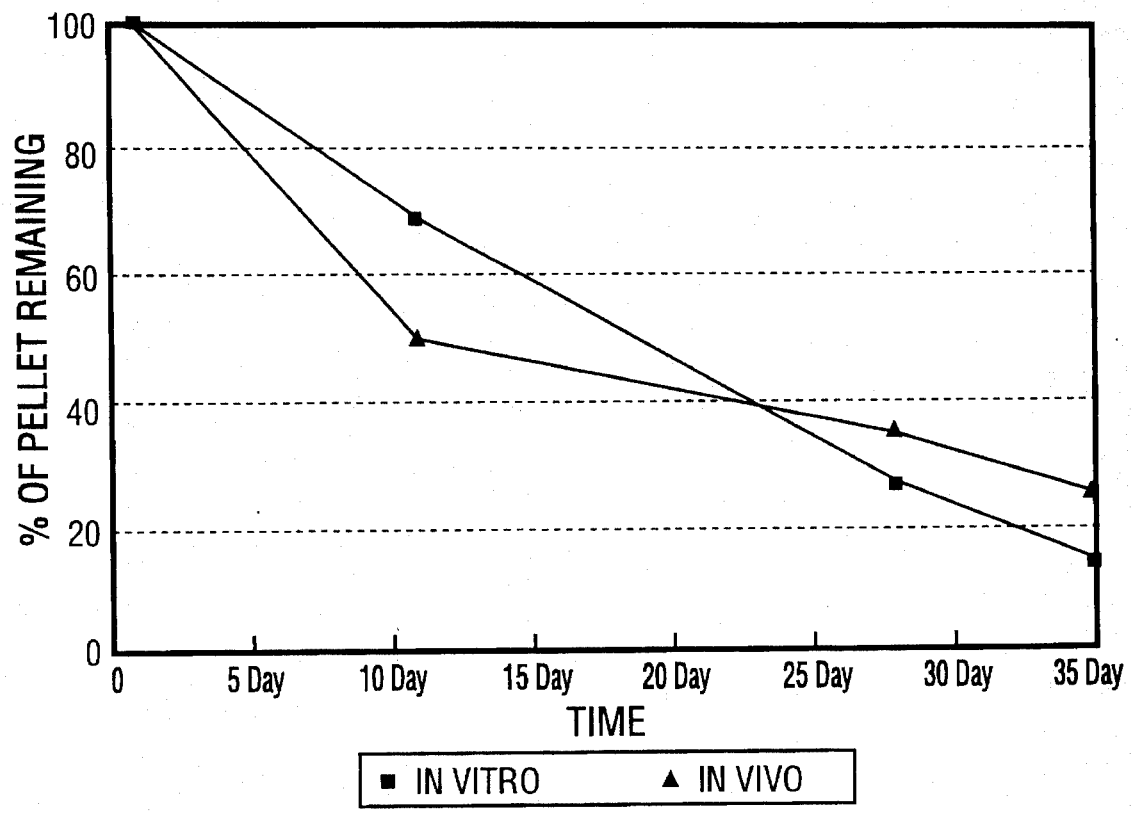
FIG. 19 shows a comparison of in vitro vs. in vivo dissolution of pellets prepared with alpha-calcium sulfate hemihydrate powder.

A comparison of these in vivo results to the in vitro results from Example 2 is shown in Table 11. The volume of the in vivo implants were approximated from the radiographic dimensions (converted to per cent remaining) and the weights of in vitro pellets are from actual measurements (converted to percent remaining), therefore, the dissolution may be plotted vs. time (FIG. 19). The correlation coefficient for the two sets of data is 0.923 indicating a relatively good correlation. These results indicate that a sustained release of a medicament in a localized area from a calcium sulfate matrix while maintaining a very low level of medication in the blood over an extended period of time is achievable.

TABLE 11

Percent of material remaining for in vivo vs. in vitro pellets

| DAY | wt. % material remaining | |
|---|---|---|
| | in vivo | in vitro |
| 1 | 100 | 100 |
| 11 | 49.8 | 75.0 |
| 28 | 34.5 | 28.7 |
| 35 | 24.4 | 16.1 |

We claim:

1. A pellet having a controllable dissolution rate, wherein said pellet comprises calcium sulfate and is prepared by the process comprising:

(a) mixing a first powder consisting essentially of alpha-calcium sulfate hemihydrate, and optionally, a second powder consisting essentially of beta-calcium sulfate hemihydrate, with a solution comprising water to form a mixture, and (b) forming said mixture into a pellet, wherein said first powder has a purity greater than 98 wt. % calcium sulfate hemihydrate, a BET surface area in the range of from about 0.4 $m^2/g$ to about 0.9 $m^2/g$, a density in the range of from about 2.73 to about 2.80 $g/cm^3$, a mean particle size of about 16 μm to about 22 μm, and wherein 90–95 wt. % of the first powder has a particle size distribution from about 1 μm to about 45 μm, wherein said second powder has a purity greater than 98 wt. % calcium sulfate hemihydrate, a BET surface area in the range of from about 4.5 $m^2/g$ to about 7.5 $m^2/g$, a density in the range of from about 2.5 $g/cm^3$ to about 2.6 $g/cm^3$, and a mean particle size in the range of from about 10 μm to about 15 μm, and wherein the dissolution rate is controlled by varying the weight ratio of the second powder to the first powder from 0 to about 3.

2. The pellet of claim 1 wherein the surface area of the powder consisting essentially of alpha-calcium sulfate hemihydrate is in the range of from about 0.4 m$^2$/g to about 0.7 m$^2$/g.

3. The pellet of claim 1 wherein the mean particle size of the powder consisting essentially of alpha-calcium sulfate hemihydrate is in the range of from about 18 μm to about 22 μm.

4. The pellet of claim 1 wherein the surface area of the powder consisting essentially of beta-calcium sulfate hemihydrate is in the range of from about 5 m$^2$/g to about 6 m$^2$/g.

5. The pellet of claim 1 wherein the mean particle size of the powder consisting essentially of beta-calcium sulfate hemihydrate is in the range of from about 13 μm to about 14 μm.

6. The pellet of claim 1 wherein the ratio of the powder consisting essentially of beta-calcium sulfate hemihydrate to the powder consisting essentially of alpha-calcium sulfate hemihydrate is in the range of from 0 to about 0.33.

7. The pellet of claim 1 wherein said pellet further comprises medicament.

8. The pellet of claim 7 wherein the medicament is an antibiotic, a chemotherapeutic agent, a growth factor, or an analgesic.

9. The pellet of claim 8 wherein said antibiotic is tetracycline hydrochloride, vancomycin, tobramycin, gentamicin or a cephalosporin.

10. The pellet of claim 8 wherein said chemotherapeutic agent is cis-platinum, ifosfamide, methotrexate, or doxorubicin hydrochloride.

11. The pellet of claim 8 wherein said growth factor is transforming growth factor beta, bone morphogenic protein, basic fiberblast growth factor, platelet-derived growth factor, or other polypeptide growth factors.

12. The pellet of claim 8 wherein said analgesic is lidocaine hydrochloride, bipivacaine hydrochloride, or ketorolac tromethamine.

13. The pellet of claim 1 wherein said solution also contains sodium chloride.

14. The pellet of claim 1 wherein the weight ratio of water to alpha-calcium sulfate hemihydrate and beta-calcium sulfate hemihydrate is in the range of from about 0.22 to about 1.

15. The pellet of claim 14 wherein the weight ratio of water to alpha-calcium sulfate hemihydrate and beta-calcium sulfate hemihydrate is in the range of from about 0.27 to 0.30.

16. The pellet of claim 6 wherein said pellet further comprises medicament.

17. The pellet of claim 16 wherein the medicament is an antibiotic, a chemotherapeutic agent, a growth factor, or an analgesic.

18. The pellet of claim 17 wherein said antibiotic is tetracycline hydrochloride, vancomycin, tobramycin, gentamicin or a cephalosporin.

19. The pellet of claim 17 wherein said chemotherapeutic agent is cis-platinum, ifosfamide, methotrexate, or doxorubicin hydrochloride.

20. The pellet of claim 17 wherein said analgesic is lidocaine hydrochloride, bipivacaine hydrochloride, or ketorolac tromethamine.

21. A method of delivering medicament in vivo comprising implanting a pellet comprising calcium sulfate and a medicament into a human or an animal, wherein said pellet is prepared by the process comprising:

(a) mixing a first powder consisting essentially of alpha-calcium sulfate hemihydrate, medicament, a solution comprising water, and, optionally, a second powder consisting essentially of beta-calcium sulfate hemihydrate, and (b) forming said mixture into a pellet, wherein said first powder has a purity greater than 98 wt. % calcium sulfate hemihydrate, a BET surface area in the range of from about 0.4 m$^2$/g to about 0.9 m$^2$/g, a density in the range of from about 2.73 to about 2.80 g/cm$^3$, a mean particle size of about 16 μm to about 22 μm, and wherein 90–95 wt. % of the first powder has a particle size distribution from about 1 μm to about 45 μm, wherein said second powder has a purity greater than 98 wt. % calcium sulfate hemihydrate, a BET surface area in the range of from about 4.5 m$^2$/g to about 7.5 m$^2$/g, a density in the range of from about 2.5 g/cm$^3$ to about 2.6 g/cm$^3$, and a mean particle size in the range of from about 10 μm to about 15 μm, and wherein the dissolution rate is controlled by varying the weight ratio of the first powder to the second powder from 0 to about 3.

22. The method of claim 21 wherein the medicament is an antibiotic, a chemotherapeutic agent, a growth factor, or an analgesic.

23. The method of claim 22 wherein said antibiotic is tetracycline hydrochloride, vancomycin, tobramycin, gentamicin or a cephalosporin.

24. The method of claim 22 wherein said chemotherapeutic agent is cis-platinum, ifosfamide, methotrexate, or doxorubicin hydrochloride.

25. The method of claim 22 wherein said growth factor is transforming growth factor beta, bone morphogenic protein, basic fiberblast growth factor, platelet-derived growth factor, or other polypeptide growth factors.

26. The method of claim 22 wherein said analgesic is lidocaine hydrochloride, bipivacaine hydrochloride, or ketorolac tromethamine.

27. The method of claim 21 wherein said solution also contains sodium chloride.

28. The method of claim 21 wherein the weight ratio of water to alpha-calcium sulfate hemihydrate and beta-calcium sulfate hemihydrate is in the range of from about 0.22 to about 1.

29. The method of claim 28 wherein the weight ratio of water to alpha-calcium sulfate hemihydrate and beta-calcium sulfate hemihydrate is in the range of from about 0.27 to 0.30.

30. A method of preparing the pellet of claim 1 wherein the mixture is formed into a pellet by subjecting the mixture to pressure.

31. A method of preparing the pellet of claim 1 wherein the mixture is formed into a pellet by molding the mixture.

* * * * *